US007869307B2

(12) United States Patent
Yamada et al.

(10) Patent No.: US 7,869,307 B2
(45) Date of Patent: Jan. 11, 2011

(54) ULTRASONIC TRANSMISSION MEMBER

(75) Inventors: Norihiro Yamada, Hino (JP); Masashi Yamada, Sagamihara (JP); Masamichi Hijino, Uenohara (JP); Nobuyuki Suda, Sagamihara (JP)

(73) Assignee: Olympus Medical Systems Corp. (JP)

(*) Notice: Subject to any disclaimer, the term of this patent is extended or adjusted under 35 U.S.C. 154(b) by 298 days.

(21) Appl. No.: 12/020,233

(22) Filed: Jan. 25, 2008

(65) Prior Publication Data

US 2009/0192388 A1 Jul. 30, 2009

(51) Int. Cl.
*A61B 8/00* (2006.01)
*B22D 23/06* (2006.01)

(52) U.S. Cl. ........................................................ 367/189

(58) Field of Classification Search ................. 367/189, 367/150, 152; 310/328
See application file for complete search history.

(56) References Cited

U.S. PATENT DOCUMENTS 5,484,398 A 1/1996 Stoddard
5,997,497 A 12/1999 Nita et al.
6,325,811 B1 12/2001 Messerly
2004/0121290 A1* 6/2004 Minevski et al. ......... 433/201.1
2009/0163836 A1* 6/2009 Sliwa ............................ 601/2
2009/0192388 A1* 7/2009 Yamada et al. .............. 600/459
2009/0193898 A1* 8/2009 Yamada et al. ................ 73/596

FOREIGN PATENT DOCUMENTS

JP 5-168645 7/1993
JP 9-323174 12/1997
JP 10-202372 8/1998
JP 2000-343205 12/2000
JP 2002-058679 2/2002
JP 2003-299666 10/2003
JP 2005-253615 9/2005
JP 2009172674 A * 8/2009

OTHER PUBLICATIONS

Information sheet prepared by applicant with relevancy statements relating to Japanese patent applications 5-168645 and 10-202372, further translations of which are not readily available.

* cited by examiner

*Primary Examiner*—Dan Pihulic
(74) *Attorney, Agent, or Firm*—Ostrolenk Faber LLP

(57) ABSTRACT

An ultrasonic transmission member including one end part and the other end part and transmitting an ultrasonic wave input into the one end part to the other end part is formed by preparing a main mold having a casting cavity corresponding to a whole outer shape of the ultrasonic transmission member, melting an alloy which is a material of a metallic glass, and pouring the melted alloy into the casting cavity of the main mold to solidify the melted alloy in a liquid phase state thereof.

8 Claims, 14 Drawing Sheets

ULTRASONIC TRANSMISSION MEMBER

BACKGROUND OF THE INVENTION

1. Field of the Invention

The present invention relates to an ultrasonic transmission member.

2. Description of the Related Art

Ultrasonic transmission members are widely used in, for example, an endoscope, an ultrasonic welding machine, or the like.

U.S. Pat. No. 6,325,811 B1 discloses an elongated ultrasonic transmission member (ultrasonic waveguide) which is inserted from a proximal end portion of an insertion part of an endoscope up to a distal end portion thereof for use, and a distal end portion of the ultrasonic transmission member is attached with a clamping arm member such that the clamping arm member is openable and closable.

U.S. Pat. No. 5,484,398 discloses an elongated hollow ultrasonic transmission member (tubular tool) which is inserted from a proximal end portion of an insertion part of an endoscope up to a distal end portion thereof for use.

Further, U.S. Pat. No. 5,997,497 discloses an elongated ultrasonic transmission member which is inserted from a proximal end portion up to a distal end portion for use in an endoscope.

Since each of these conventional ultrasonic transmission members must have a high dimensional precision in order to transmit an ultrasonic wave from its one end to its another end efficiently and since they need corrosion resistance, they are formed by machining a metal material, such as titanium, titanium alloy, aluminum alloy, or nickel-aluminum alloy.

Machining of these metal materials with high dimensional precision needs much time required for forming the conventional ultrasonic transmission member and increases its forming cost.

Metallic glass attracts attention as a material which does not include a crystal grain boundary and which is therefore excellent in corrosion resistance, strength, elastic modulus, formability, and shape transfer property, as compared with the metal materials. For example, Japanese Patent Application KOKAI publication No. 10-202372 discloses that two or more members are integrally joined to each other by using metallic glass. Japanese Patent Application KOKAI publication No. 2000-343205 discloses that metallic glass is formed in a cylindrical shape in a supercooled liquid region thereof. Further, Japanese Patent Application KOKAI publication No. 09-323174 discloses that two or more members are integrally joined to each other by using metallic glass.

The metallic glass is a kind of amorphous alloy obtained by melting a plurality of (at least three) crystalline metals by utilizing arc-discharge or the like to produce an alloy and then cooling the alloy rapidly, and has a supercooled liquid region (glass transition temperature zone) of a predetermined temperature range. The metallic glass exhibits an excellent shape transfer property in the supercooled liquid region (glass transition temperature zone), similarly to forming glass while it is softened by heating. When rapid cooling is performed after the plurality of crystalline metals are melted to be alloyed as described above, the melted alloy is poured into a casting cavity of a mold so that the shape and dimensions of the casting cavity of the mold can be transferred precisely, as in a case where melted glass is poured into a casting cavity of a mold. For example, a charging rate of metallic glass of an Ni group is as high as about 99%, as compared with that the charging rate of an ordinary aluminum alloy for die-casting to a predetermined casting cavity of a predetermined mold is about 84%.

The plurality (at least three kinds) of crystalline metals are different from each other in their element dimensions, and, after they are alloyed as described above, they are not arranged regularly so that they are not crystallized. The plurality (at least three kinds) of crystalline metals after they are alloyed have an energy amount less than that before they are alloyed, so that they are mixed more easily. Various amorphous alloys having a property which can be called as a "metallic glass" have been known, and for example $Zr_{55}Cu_{30}Al_{10}Ni_5$ comprising four kinds of metals of Zr, Cu, Al, and Ni is relatively widely known.

This amorphous alloy can be obtained by melting four kinds of metals of Zr, Cu, Al, and Ni at a temperature of about 1200° C. and then cooling the melted metals rapidly at a cooling rate of 10 K/sec or more, and, in this amorphous alloy, a temperature range between about 400° C. and about 450° C. is a supercooled liquid region (glass transition temperature zone).

In addition to the excellent shape transfer property and formability as described above, metallic glass has a low Young's modulus equivalent to that of a conventional crystalline alloy such as magnesium alloy, duralumin, titanium alloy, stainless steel, or ultrahigh tensile strength steel and is considerably superior in tensile strength to the conventional crystalline alloy. Further, metallic glass has a corrosion resistance of at least 10000 times that of conventional stainless steel.

BRIEF SUMMARY OF THE INVENTION

According to one aspect of the present invention, an ultrasonic transmission member including one end part and the other end part and transmitting an ultrasonic wave input into the one end part to the other end part, is formed by preparing a main mold having a casting cavity corresponding to a whole outer shape of the ultrasonic transmission member, and by melting an alloy which is a material of a metallic glass and pouring the melted alloy into the casting cavity of the main mold to solidify the melted alloy in a liquid phase state thereof to be changed to the metallic glass.

According to another aspect of the present invention, an ultrasonic transmission member including one end part and the other end part and transmitting an ultrasonic wave input into the one end part to the other end part, is formed by preparing an ultrasonic transmission member main body having a whole shape of desired dimensions for ultrasonic transmission except for a predetermined area, by preparing a predetermined area formation mold having a casting cavity corresponding to an outer shape of the predetermined area, by placing an area of the ultrasonic transmission member main body adjacent to the predetermined area in the casting cavity of the predetermined area formation mold, and by melting an alloy which is a material of a metallic glass and pouring the melted alloy into the casting cavity and solidifying the melted alloy in a liquid phase state thereof to change the melted alloy to the metallic glass, so that the predetermined area is joined to the adjacent area of the ultrasonic transmission member main body by the metallic glass.

According to a further aspect of the present invention, an ultrasonic transmission member including one end part and the other end part and transmitting an ultrasonic wave input into the one end part to the other end part, is formed by preparing a mold formed with a casting cavity corresponding to a whole outer shape of the ultrasonic transmission member, by preparing a U-shaped pipe extending from the one end part of the ultrasonic transmission member to the other end part thereof and returning back to the one end part, by disposing the U-shaped pipe in the casting cavity of the mold such that both end parts of the U-shaped pipe are projected from one end part of the casting cavity and a bent part of the U-shaped pipe is positioned in the casting cavity, and by melting an alloy which is a material of a metal glass pouring the melted alloy into the casting cavity of the mold and solidifying the melted alloy in a liquid phase state thereof to change the melted alloy to the metallic glass, so that an ultrasonic transmission member accompanying the U-shaped pipe therein is formed with the metallic glass.

According to more further aspect of the present invention, an ultrasonic transmission member with an elongated shape having a predetermined length, including one end part and the other end part, and transmitting an ultrasonic wave input into the one end part to the other end part, is formed by preparing a mold formed with a casting cavity of an ultrasonic transmission member block corresponding to a whole outer shape of the ultrasonic transmission member except that a length of the ultrasonic transmission member block is shorter than the predetermined length, by melting an alloy which is a material of a metal glass, pouring the melted alloy into the casting cavity of the mold, and solidifying the melted alloy in a liquid phase state thereof to change the melted alloy to the metallic glass, so that the ultrasonic transmission member block is formed with the metallic glass, and by pulling the ultrasonic transmission member block up to the predetermined length while a predetermined area of the ultrasonic transmission member block between the one end part of the ultrasonic transmission member block and the other end thereof in a longitudinal direction thereof is heated up to a supercooled liquid region of the metallic glass and is kept in the supercooled liquid region.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

At first, a method for forming an ultrasonic transmission member according to a first embodiment of the present invention will be explained with reference to FIGS. 1A to 1C.

Figure 1A:
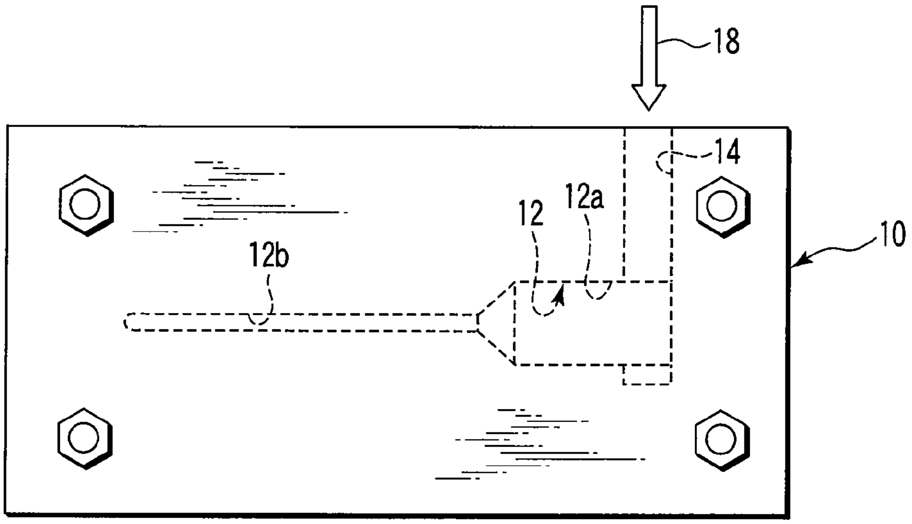
FIG. 1A is a schematic side view of a main mold used for a method for forming an ultrasonic transmission member according to a first embodiment of the present invention.
Figure 1B:
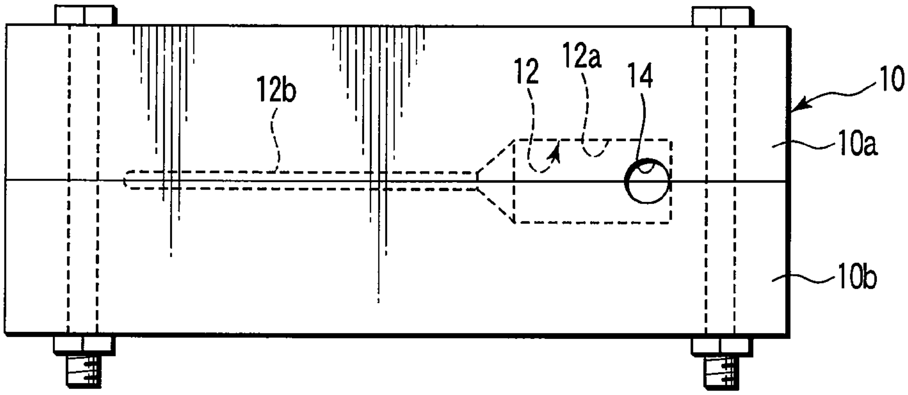
FIG. 1B is a schematic top view of the main mold shown in FIG. 1A.

As shown in FIGS. 1A and 1B, a main mold 10 having a casting cavity 12 is prepared. The main mold 10 further has a melted material inflow passage (runner channel) 14 for causing the casting cavity 12 to communicate with an external space. The casting cavity 12 has a shape corresponding to a whole outer shape and outer dimensions of a desired ultrasonic transmission member 16 illustrated in FIG. 1C.

In this embodiment, the desired ultrasonic transmission member 16 includes one end part 16*a* with a large diameter and the other end part 16*b* with a small diameter and configures an elongated ultrasonic probe transmitting an ultrasonic wave input into the one end part 16*a* to the other end part 16*b*. A connection tool 16*c* for connecting the ultrasonic transmission member 16 to an ultrasonic generator (not shown) is formed on a side of the one end part 16*a* with a large diameter which is opposite to the other end part 16*b*. In this embodiment, the connection tool 16*c* is a male screw.

An ultrasonic wave with a predetermined frequency is input from the ultrasonic generator (not shown) connected to the connection tool 16*c* into the one end part 16*a* of the ultrasonic transmission member 16, and it is preferable that a length L from an end surface of the one end part 16*a* with a large diameter on a side opposite to the other end part 16*b* with a small diameter to a terminal end of the other end part 16*b* is integer times of a half (λ/2) of one wavelength λ of the ultrasonic wave. Such an ultrasonic transmission member 16 is used in an endoscopic operation, for example.

Further, it is preferable that an end of the one end part 16*a* with a large diameter of the ultrasonic transmission member 16 positioned on a side of the other end part 16*b* with a small diameter (that is, a starting position of transition from the one end part 16*a* with a large diameter to the other end part 16*b* with a small diameter on an outer peripheral surface of the ultrasonic transmission member 16) substantially coincides with a node of the ultrasonic wave input from the ultrasonic generator (not shown) connected to the connection tool 16*c* into the one end part 16*a* of the ultrasonic transmission member 16.

The casting cavity 12 in the embodiment includes a one end part corresponding portion 12*a* corresponding to the one end part 16*a* with a large diameter of the ultrasonic transmission member 16 and an other end part corresponding portion 12*b* corresponding to the other end part 16*b* with a small diameter of the ultrasonic transmission member 16.

The main mold 10 is a laterally divided type having divided surfaces spreading in a vertical direction, and is formed with a metal having a high thermal conductivity, such as copper. Two half lateral pieces 10*a* and 10*b* of the main mold 10 have shapes symmetrical to each other, and they are fixed to each other in a separable manner by a known separable fixing structure, for example, combinations of bolts and nuts. The casting cavity 12 and the melted material inflow passage (runner channel) 14 are formed in the divided surfaces of the two half lateral pieces 10*a* and 10*b* of the main mold 10 in a vertically divided manner.

The melted material inflow passage (runner channel) 14 has an outer end (pouring gate) opened in an upper surface of the main mold 10 and an inner end connected to a predetermined portion of the casting cavity 12, a side of the one end part corresponding portion 12*a* opposite to the other end part corresponding portion 12*b* in this embodiment.

A melted alloy 18 including at least three elements and being a material of metallic glass is poured into the outer end (pouring gate) of the melted material inflow passage (runner channel) 14. In this embodiment, the three elements include at least one of Ti, Zr, and Al. An acoustic impedance of Al is low (14 $Gpa \cdot s/m^3$) and an acoustic impedance of Ti is not as low as that of Al but is low (21 $Gpa \cdot s/m^3$). However, a mechanical quality factor Q and a mechanical strength of Ti are high. Zr increases an amorphous forming ability and expands a supercooled liquid region (glass transition temperature zone) of metallic glass. In general, a material with a lower acoustic impedance and higher mechanical quality factor Q has a lower loss in a vibration transmission.

Specifically, the alloy 18 which is the material of the metallic glass used in the embodiment is $Zr_{55}Cu_{30}Al_{10}Ni_5$. However, various known alloys which are materials of a metallic glass may be used as long as a desired formation of the ultrasonic transmission member 16 and a desired performance of the formed ultrasonic transmission member 16 can be obtained. Such alloys which are the materials of a metallic glass may include $Zr_{60}Cu_{30}Al_{10}$, $Ti_{53}Cu_{30}Ni_{15}Co_2$, $Al_{10}Ni_{15}La_{65}Y_{10}$, $Ti_{53}Cu_{15}Ni_{18.5}Hf_3Al_7Si_3B_{0.5}$, $Ti_{40}Zr_{10}Cu_{36}Pd_{14}$, $Ti_{53}Cu_{15}Ni_{18.5}Zr_3Al_7Si_3B_{0.5}$, and the like.

Various known heat-radiating and/or cooling structures (not shown) are applied to the main mold 10 to solidify the melted alloy 18, which is the material of the metallic glass and which has been poured into the casting cavity 12 through the melted material inflow passage (runner channel) 14, in a liquid phase state thereof. As a result, the melted alloy 18 which has been poured into the casting cavity 12 is cooled at a cooling rate of 10 K/sec or more. Since the melted alloy 18 which has been poured into the casting cavity 12 is rapidly cooled in this manner and is changed to an amorphous alloy (so-called "metallic glass") where a crystalline grain boundary is not present, so that a shape and dimensions of the casting cavity 12 are transferred to the amorphous alloy (so-called "metallic glass") precisely.

The ultrasonic transmission member 16 formed with the metallic glass which has became a glass solidification region in the casting cavity 12 and which has been transferred with the shape of the casting cavity 12, is taken out of the main mold 10 after further heat radiation for a predetermined time. At this time, the ultrasonic transmission member 16 on which the shape of the casting cavity 12 is transferred as shown by a solid line in FIG. 1C, includes a melted material inflow passage corresponding portion 14*a* having a shape corresponding to the melted material inflow passage (runner channel) 14 on a side of the one end part 16*a* with a large diameter opposite to the other end part 16*b* as shown by a two-dots chain line in FIG. 1C.

Next, a connection tool 16*c* is formed by machining the melted material inflow passage corresponding portion 14*a*. During this machining work, various known cooling actions, such as application of a cooling medium including a cooling liquid, must be applied not to reach a temperature of the metallic glass of the melted material inflow passage corresponding portion 14*a* to a crystallization temperature or higher (that is, the metallic glass keeps amorphous and is not crystallized).

Here, technical merits obtained by forming the ultrasonic transmission member 16 with the metallic glass will be described below.

Since the metallic glass is superior to conventional metal materials used for forming an ultrasonic transmission member, such as titanium, titanium alloy, aluminum alloy, or nickel-aluminum alloy in a formability and a shape transfer property, even if the ultrasonic transmission member has a complicated shape, the substantially whole ultrasonic transmission member can be formed with a high dimensional precision only by casting so that a forming cost of the ultrasonic transmission member can be reduced.

Since the metallic glass is amorphous and does not include any crystalline grain boundaries, it is excellent in acoustic characteristics. Since an ordinary metal includes crystalline grain boundaries, when an ultrasonic wave is applied to the ordinary metal, reflection of the ultrasonic wave occurs and a loss of ultrasonic vibration energy occurs.

Since a tensile strength of the metallic glass is considerably superior to that of the ordinary metal, for example, it is three times of that of a Ti alloy, an ultrasonic transmission member is not destroyed easily by a vibration stress occurring in the ultrasonic transmission member when an ultrasonic wave is applied to the ultrasonic transmission member.

Since the metallic glass is amorphous and does not include any crystalline grain boundaries, it is excellent in corrosion resistance.

In the abovementioned embodiment, the melted alloy 18 which is the material of the metallic glass is poured into the outer end (pouring gate) of the melted material inflow passage (runner channel) 14 by the gravity, but it may be poured into the outer end (pouring gate) of the melted material inflow passage (runner channel) 14 in a state that the melted alloy 18 has been applied with a pressure by a known pressurizing mechanism.

First Modification of First Embodiment

Next, a first modification of the method for forming an ultrasonic transmission member according to the first embodiment of the present invention will be explained with reference to FIGS. 2A to 2C.

This modification is different from the method for forming an ultrasonic transmission member according to the first embodiment of the present invention and described with reference to FIGS. 1A to 1C in the following manner. That is, a casting cavity 12' formed in the main mold 10 to correspond to an outer shape of the ultrasonic transmission member 16 includes a connection tool corresponding portion 12*c* corresponding to an outer shape of a connection tool 16' of the ultrasonic transmission member 16 on a side of the one end part corresponding portion 12*a* opposite to the other end part corresponding portion 12*b*, and the inner end of the melted material inflow passage (runner channel) 14 is connected to a side of the connection tool corresponding portion 12*c* opposite to the one end part corresponding portion 12*a*.

The melted alloy 18 which is the material of the metallic glass is poured into the outer end (pouring gate) of the melted material inflow passage (runner channel) 14, and the melted alloy 18 charged in the casting cavity 12' is rapidly cooled to be changed to the metallic glass in the glass solidification range, so that the metallic glass transferred with the shape of the casting cavity 12 configures the ultrasonic transmission member 16. When the ultrasonic transmission member 16 is taken out form the main mold 10 after further heat radiation for a predetermined time period as shown by a solid line in FIG. 2C, the connection tool 16'C accompanies a melted material inflow passage corresponding portion 14*a* having a shape corresponding to the melted material inflow passage (runner channel) 14 on a side of the connection tool 16'C opposite to the one end part 16*a* with a large diameter, as shown by a two dots chain line in FIG. 2C.

Accordingly, the melted material inflow passage corresponding portion 14*a* is finally removed from the connection tool 16'C by machining.

Figure 1C:
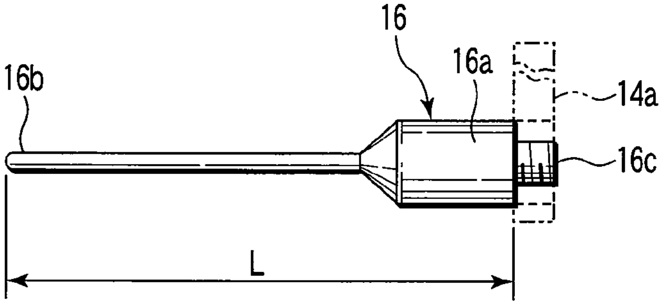
FIG. 1C is a schematic side view of an ultrasonic transmission member formed with metallic glass by using the main mold schematically shown in FIGS. 1A and 1B.
Figure 2A:
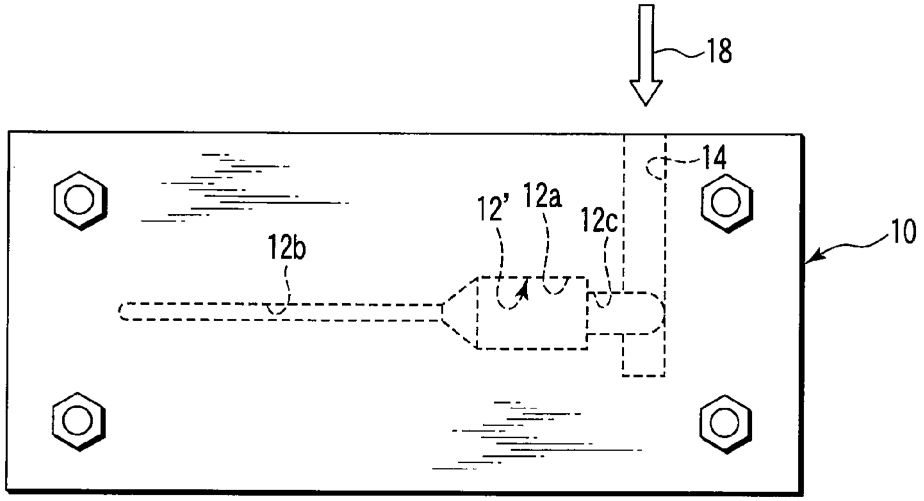
FIG. 2A is a schematic side view of a main mold used for a first modification of the method for forming an ultrasonic transmission member according to the first embodiment of the present invention.
Figure 2B:
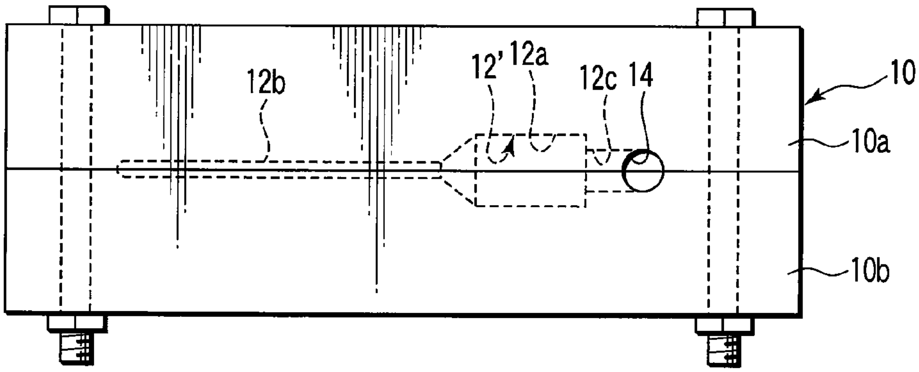
FIG. 2B is a schematic top view of the main mold shown in FIG. 2A.
Figure 2C:
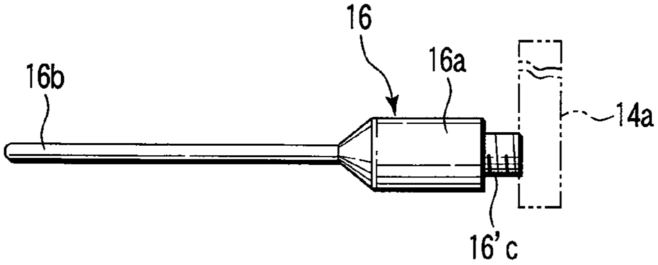
FIG. 2C is a schematic side view of an ultrasonic transmission member formed with metallic glass by using the main mold schematically shown in FIGS. 2A and 2B.

The performance of the ultrasonic transmission member 16 which is formed by the first modification of the method for forming an ultrasonic transmission member according to the first embodiment of the present invention and which is described with reference to FIGS. 2A to 2C, is the same as the performance of the ultrasonic transmission member 16 which is formed by the method for forming an ultrasonic transmission member according to the first embodiment of the present invention and which is described with reference to FIGS. 1A to 1C. However, when the ultrasonic transmission member 16 is formed by the first modification of the method for forming an ultrasonic transmission member according to the first embodiment, machining for the connection tool 16*c* is made unnecessary.

Second Modification of First Embodiment

Figure 3A:
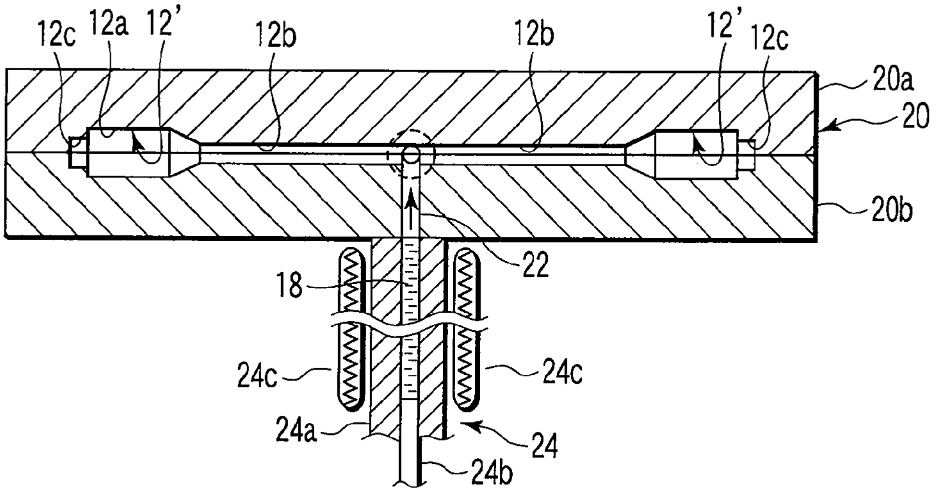
FIG. 3A is a schematic vertical sectional view of a main mold used for a second modification of the method for forming an ultrasonic transmission member according to the first embodiment of the present invention.
Figure 3B:
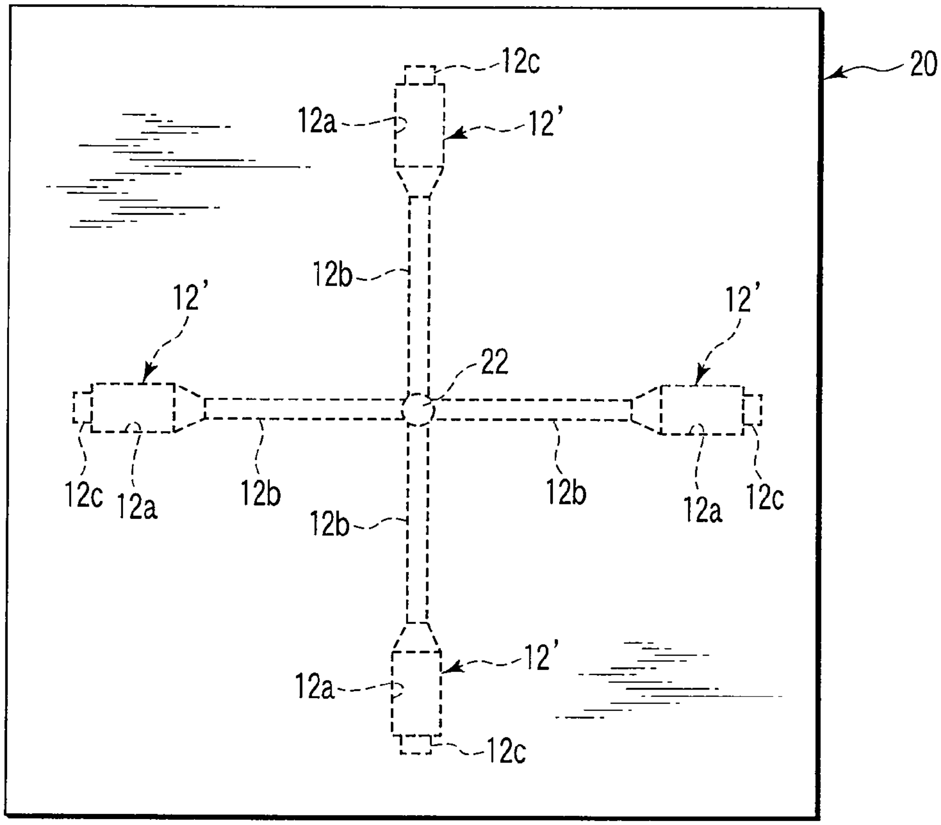
FIG. 3B is a schematic top view of the main mold shown in FIG. 3A.

Next, a second modification of the method for forming an ultrasonic transmission member according to the first embodiment of the present invention will be explained with reference to FIGS. 3A and 3B.

The modification is different from the method for forming an ultrasonic transmission member according to the first embodiment of the present invention and described with reference to FIGS. 1A to 1C in the following manner.

That is, a main mold 20 formed with a plurality of casting cavities 12', each being the same as the casting cavity 12' formed in the main mold 10 used in the first modification of the method for forming an ultrasonic transmission member according to the first embodiment of the present invention and described with reference to FIGS. 2A to 2C, is prepared.

The main mold 20 is an upper and lower divided type having divided surfaces spreading in a horizontal direction, and is formed with a metal having a high thermal conductivity, such as copper. Upper and lower half pieces 20*a* and 20*b* of the main mold 20 are fixed to each other in a separable manner by a known separable fixing structure, for example, combinations of bolts and nuts. A plurality of casting cavities 12' are formed in the divided surfaces of the upper and lower half pieces 20*a* and 20*b* of the main mold 20 in a horizontally partitioned manner.

In the main mold 20, the plurality of casting cavities 12' are disposed radially in a state that free ends of the other end part corresponding portions 12*b* each having a small diameter are collected at one point, and a melted material inflow passage (runner channel) 22 having an inner end positioned at the one point and an outer end (pouring gate) opened in a lower surface of the lower half piece 20*b* is formed in the lower half piece 20*b*. The inner end of the melted material inflow passage (runner channel) 22 communicates with the free ends of the other end part corresponding portions 12*b* each having a small diameter of the plurality of casting cavities 12'.

The outer end (pouring gate) of the melted material inflow passage (runner channel) 22 is connected with an injection port of a known melted metal pressurizing-injecting mechanism 24 holding the melted alloy 18 which is the material of the metallic glass. The melted metal pressurizing-injecting mechanism 24 injects the melted alloy 18 from the injection port thereof into the plurality of casting cavities 12' through the melted material inflow passage (runner channel) 22 under a predetermined pressure.

The melted metal pressurizing-injecting mechanism 24 includes a cylinder 24*a* having an inner hole holding the melted alloy 18, a piston 24*b* accommodated in the inner hole of the cylinder 24*a* to be slidable to push out the melted alloy 18 toward the injection port by the predetermined pressure, and heaters 24*c* for keeping the temperature of the melted alloy 18 held in the inner hole of the cylinder 24*a* at the melting point of the melted alloy 18 or higher.

The melted material inflow passage (runner channel) 22 may be formed in the upper half piece 20*a* of the main mold 20. In this case, if the melted alloy 18 can be poured into the plurality of casting cavities 12' through the melted material inflow passage (runner channel) 22 without forming blowholes in each of the plurality of casting cavities 12', the melted alloy 18 can be poured into the outer port (pouring gate) of the melted material inflow passage (runner channel) 22 by utilizing only the gravity without using the melted metal pressurizing-injecting mechanism 24.

Further, if the melted alloy 18 can be poured into each of the plurality of casting cavities 12 through the melted material inflow passage (runner channel) 22 without forming blowholes in each of the plurality of casting cavities 12, the plurality of casting cavities 12' can be disposed in the main mold 20 in various arrangements other than the radial arrangement.

Instead of the same casting cavity 12' as the casting cavity 12' formed in the main mold 10 in the first modification of the method for forming an ultrasonic transmission member according to the first embodiment of the present invention and described with reference to FIGS. 2A to 2C, the same casting cavity 12 as the casting cavity 12 formed in the main mold 10 in the method for forming an ultrasonic transmission member according to the first embodiment of the present invention and described with reference to FIGS. 1A to 1C can be used.

Various known heat radiation and/or cooling structures (not shown) are applied to the main mold 20 to make the melted alloy 18, which is the material of the metallic glass and which has been poured into the casting cavities 12' through the melted material inflow passage (runner channel) 22, being solidified in a liquid-phase state thereof. As a result, the melted alloy 18 which has been poured into the casting cavities 12' is cooled at a cooling rate of 10 K/sec or more. The melted alloy 18 which has been poured into the casting cavities 12' is cooled in this manner to form an amorphous alloy (so-called "metallic glass") where no crystalline grain boundaries are present, so that the shape and the dimensions of the casting cavities 12' are transferred to the amorphous alloy (so-called "metallic glass") precisely.

Third Modification of First Embodiment

Next, a third modification of the method for forming an ultrasonic transmission member according to the first embodiment of the present invention will be explained with reference to FIGS. 4A to 4C.

A method for forming an ultrasonic transmission member according to the third modification includes forming a predetermined area of the ultrasonic transmission member 16 in a desired shape after the ultrasonic transmission member 16 has been formed by the method for forming an ultrasonic transmission member according to the first embodiment of the present invention and described with reference to FIGS. 1A to 1C, by the first modification of the method for forming an ultrasonic transmission member according to the first embodiment and described with reference to FIGS. 2A to 2C, or by the second modification of the method for forming an ultrasonic transmission member according to the first embodiment of the present invention and described with reference to FIGS. 3A and 3B.

In the following explanation, the predetermined area of the ultrasonic transmission member 16 is a distal end portion EP of the other end part 16*b* with a small diameter.

Figure 4A:
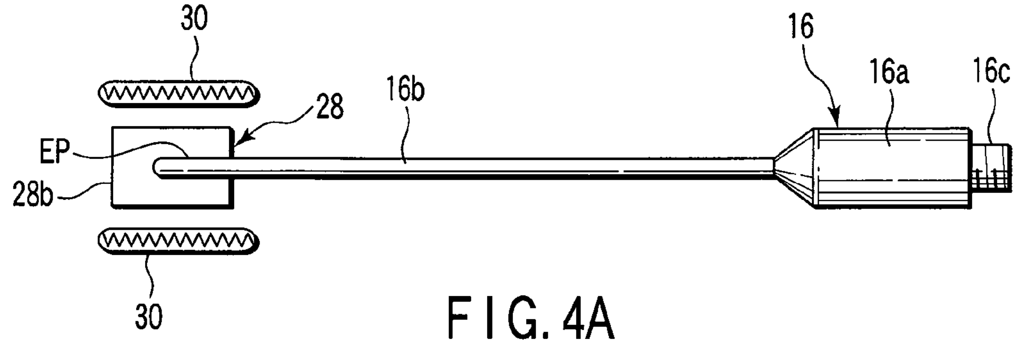
FIG. 4A is a schematic side view showing a sub-mold with heaters used in a third modification of the method for forming an ultrasonic transmission member according to the first embodiment of the present invention, and showing an ultrasonic transmission member having a distal end portion of an other end part with a small diameter as a predetermined area to which a desired shape of a casting cavity of the sub-mold is transferred.
Figure 4B:
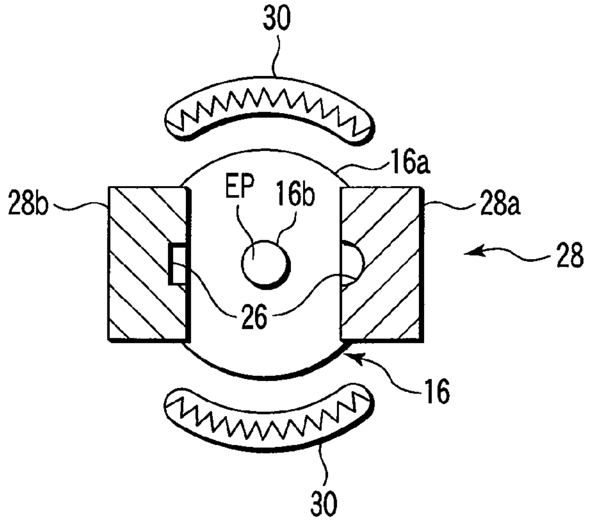
FIG. 4B is a schematic front view showing the sub-mold and the distal end portion of the other end part with a small diameter of the ultrasonic transmission member shown in FIG. 4A, where only the sub-mold is sectioned.

Therefore, in the third modification, a sub-mold 28 having a predetermined casting cavity 26 corresponding to the desired shape is prepared, as shown in FIGS. 4A and 4B.

In this modification, the sub-mold 28 is a laterally divided type, has divided surfaces spreading vertically, and is formed with a metal such as copper. Two half lateral pieces 28*a* and 28*b* of the sub-mold 28 are supported by a known opening and closing mechanism (not shown) so as to join with and separate from each other. The predetermined casting cavity 26 is formed in the divided surfaces of the half lateral pieces 28*a* and 28*b* in a vertically divided manner.

Heaters 30 are disposed in the sub-mold 28 and/or around the sub-mold 28.

When the half lateral pieces 28*a* and 28*b* of the sub-mold 28 are separated from each other and the distal end portion EP of the other end part 16*b* with a small diameter of the ultrasonic transmission member 16 is placed into the casting cavity 26 of the sub-mold 28 as shown in FIG. 4B, the distal end portion EP is heated by the heaters 30 up to a temperature of the supercooled liquid region (glass transition zone) of the metallic glass forming the ultrasonic transmission member 16 and the temperature is maintained, before the half lateral pieces 28*a* and 28*b* of the sub-mold 28 are closed.

Figure 4C:
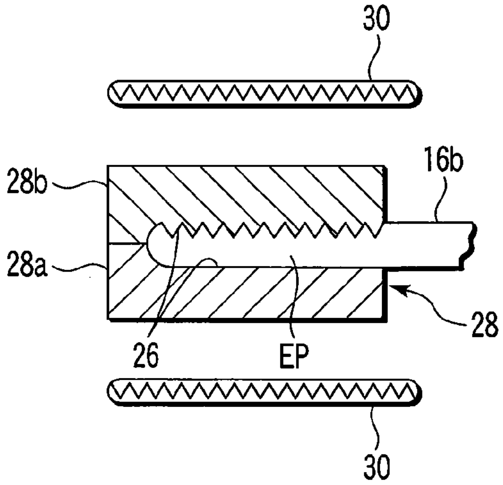
FIG. 4C is a schematic enlarged side view showing the vertically cut sub-mold and the distal end portion of the other end part with a small diameter of the ultrasonic transmission member shown in FIG. 4A, in a state that an outer shape of the casting cavity has been transferred to the distal end portion of the other end part with a small diameter of the ultrasonic transmission member by the casting cavity of the sub-mold.

Next, the half lateral pieces 28*a* and 28*b* of the sub-mold 28 are closed, the casting cavity 26 of the sub-mold 28 are pressed onto the metallic glass of the distal end portion EP whose temperature is maintained in the supercooled liquid region (glass transition zone) as shown in FIG. 4C, and the desired shape of the casting cavity 26 of the sub-mold 28 is transferred to the metallic glass of the distal end portion EP.

Thereafter, after activation of the heaters 30 is stopped and the temperature of the metallic glass of the distal end portion EP drops under the glass transition temperature Tg, namely it becomes the glass solidification temperature, the half lateral pieces 28*a* and 28*b* of the sub-mold 28 are opened so that the distal end portion EP of the other end part 16*b* with a small diameter of the ultrasonic transmission member 16 is taken out from the casting cavity 26 of the sub-mold 28.

Thus, the distal end portion EP of the other end part 16*b* with a small diameter of the ultrasonic transmission member 16, which has been transferred with the outer shape of the casting cavity 26 of the sub-mold 28, can be transformed to another desired shape corresponding to an outer shape of another desired and predetermined casting cavity of another sub-mold by using the another sub-mold while the distal end portion EP of the ultrasonic transmission member 16 is heated up to a temperature in the supercooled liquid region again and the temperature is maintained.

Second Embodiment

Next, a method for forming an ultrasonic transmission member according to a second embodiment of the present invention will be explained with reference to FIGS. 5A to 5E.

Figure 5A:
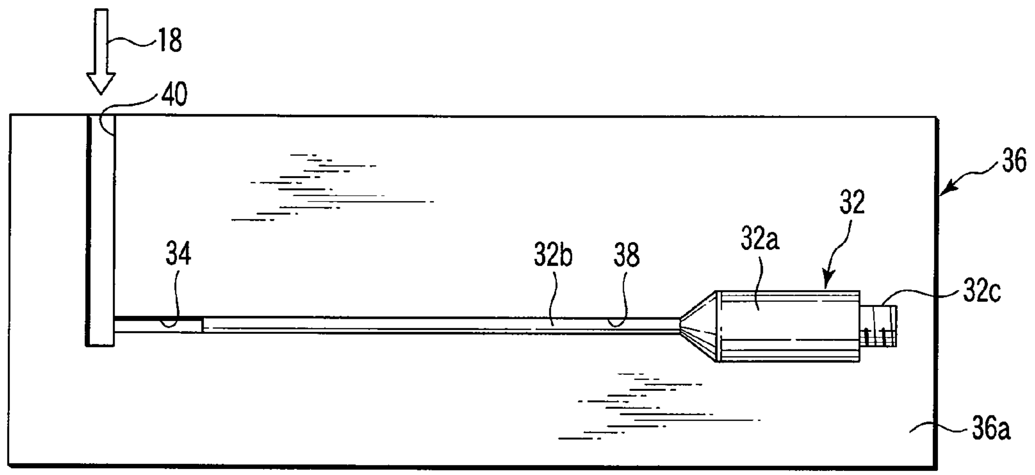
FIG. 5A is a schematic side view of a half lateral piece of a primary formation mold used for a method for forming an ultrasonic transmission member according to a second embodiment of the present invention and an ultrasonic transmission member main body disposed in a half casting cavity of the half lateral piece.

At first in this method, as shown in FIG. 5A, an ultrasonic transmission member main body 32 having a whole shape and desired dimensions for ultrasonic transmission except for a predetermined area is prepared and also a predetermined area forming mold 36 having a casting cavity 34 corresponding to an outer shape of the predetermined area is prepared.

The predetermined area forming mold 36 is a laterally divided type having divided surfaces spreading in a vertical direction, and is formed with a metal having high heat conductivity such as copper. Two half lateral pieces 36*a* of the predetermined area forming mold 36 are fixed to each other in a separable manner by a known separable fixing structure, for example, combinations of bolts and nuts. The two half lateral pieces 36*a* have symmetrical shapes to each other, and only one of the half lateral pieces 36*a* is shown in FIG. 5A. The casting cavity 34 is formed in the divided surfaces of the two half lateral pieces 36*a* of the predetermined area forming mold 36 in a vertically divided manner.

In this embodiment, the ultrasonic transmission member main body 32 has one end part 32*a* with a large diameter and the other end part 32*b* with a small diameter. The ultrasonic transmission member main body 32 configures an elongated ultrasonic probe block transmitting an ultrasonic wave input into the one end part 32*a* up to the other end part 32*b*, and a final product of an elongated ultrasonic probe having a whole shape with desired dimensions for ultrasonic transmission is obtained by further connecting the predetermined area to a distal end of the other end part 32*b*.

A connection tool 32*c* for connecting an ultrasonic generator (not shown) is formed on a side of the one end part 32*a* with a large diameter opposite to the other end part 16*b* in the ultrasonic transmission member main body 32. In this embodiment, the connection tool 32*c* is a male screw.

Figure 5B:
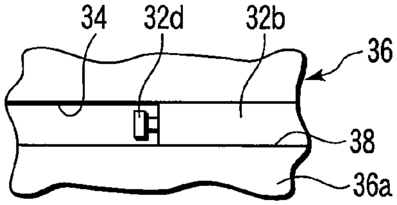
FIG. 5B is an enlarged side view schematically showing a distal end portion of the other end part with a small diameter which is a predetermined area of the ultrasonic transmission member main body disposed in the half casting cavity of the half lateral piece shown in FIG. 5A.

As shown in FIG. 5B, an anchor structure 32*d* is formed on the distal end of the other end part 32*b* (namely, a portion adjacent to the predetermined area) of the ultrasonic transmission member main body 32 to be connected with the predetermined area formed by the casting cavity 34 of the predetermined area forming mold 36 and fixed to the anchor structure 32*d*. In this embodiment, the anchor structure 32*d* includes a shank with a small diameter projecting from the distal end of the other end part 32*b* concentrically and an umbrella with an expanded diameter at a distal end of the shank. However, the anchor structure 32*d* takes various known shapes as long as it can be fixed with the predetermined area formed at the distal end of the other end part 32*b* of the ultrasonic transmission member main body 32 by the casting cavity 34 of the predetermined area forming mold 36.

The ultrasonic transmission member main body 32 is formed by machining a metal material such as titanium, titanium alloy, aluminum alloy, or nickel-aluminum alloy, as used in an ultrasonic probe conventionally used in an endoscopic operation.

The predetermined area formation mold 36 also has an ultrasonic transmission member main body accommodating space 38 having the same outer shape as that of the ultrasonic transmission member main body 32, for accommodating the ultrasonic transmission member main body 32. The ultrasonic transmission member main body accommodating space 38 is also formed in the divided surfaces of the two half lateral pieces 36*a* of the predetermined area forming mold 36 in a vertically divided manner. The casting cavity 34 is configured in an elongated shape as an area extending from the distal end of the other end part 32*b* with a small diameter of the ultrasonic transmission member main body 32 in the ultrasonic transmission member main body accommodating space 38.

An inner end of a melted material inflow passage (runner channel) 40 formed in the predetermined area forming mold 36 communicates with the casting cavity 34 on a side opposite to the ultrasonic transmission member main body accommodating space 38. The melted material inflow passage (runner channel) 40 is also formed in the divided surfaces of the two half lateral pieces 36*a* of the predetermined area formation mold 36 in a vertically divided manner.

The melted alloy 18 which is the material of the metallic glass is poured into an outer end (pouring gate) of the melted material inflow passage (runner channel) 40. The melted alloy 18 can be poured into the outer end (pouring gate) of the melted material inflow passage (runner channel) 40 by the gravity or by the melted metal pressurizing-injecting mechanism 24 used in the second modification of the method for forming an ultrasonic transmission member according to the first embodiment of the present invention described with reference to FIGS. 3A and 3B.

Various known heat-radiation and/or cooling structures (not shown) are applied to the predetermined area formation mold 36 so that the melted alloy 18, which is the material of the metal alloy and which has been poured into the casting cavity 34 through the melted material inflow passage (runner channel) 40 is solidified in a liquid-phase state thereof. As a result, the melted alloy 18 poured into the casting cavity 34 is cooled at a cooling rate of 10 K/sec or more. The melted alloy 18 poured into the casting cavity 34 is cooled rapidly in this manner to be changed to an amorphous alloy (so-called "metallic glass") where no crystalline grain boundary is present, so that the shape and the dimensions of the casting cavity 34 are transferred to the amorphous alloy (so-called "metallic glass") precisely.

A predetermined area 42 formed with metallic glass, whose temperature has been lowered to the glass solidification range in the casting cavity 34 and which has been transferred with the shape of the casting cavity 34, is taken out from the predetermined area formation mold 36 after further heat radiation for a predetermined time. At this time, as shown by a solid line in FIG. 5C, the predetermined area 42 has been connected to the distal end of the other end part 32*b* with a small diameter of the ultrasonic transmission member main body 32 by the anchor structure 32*d*. A melted material inflow passage corresponding portion (not shown) with a shape corresponding to the melted material inflow passage (runner channel) 40 is attached to the predetermined area 42, but the melted material inflow passage corresponding portion is cut off from the predetermined area 42 by a known cut-off mechanism.

Figure 5C:
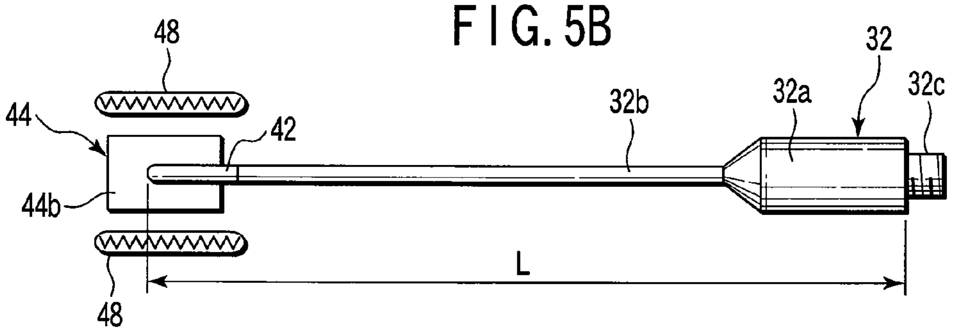
FIG. 5C is a side view schematically showing the ultrasonic transmission member main body after a partial block for secondary formation has been formed at the distal end portion of the other end part with a small diameter which is the predetermined area by the primary formation mold shown in FIG. 5A, and a secondary formation mold with heaters used for secondary formation of the partial block of the ultrasonic transmission member main body.
Figure 5D:
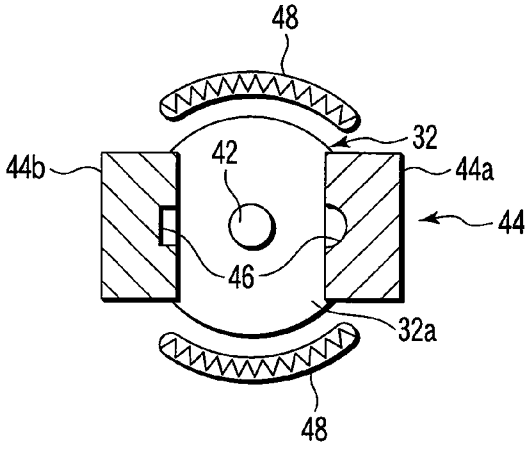
FIG. 5D is a schematic front view showing the secondary formation mold and the partial block of the distal end portion of the other end part with a small diameter of the ultrasonic transmission member shown in FIG. 5C, where only the secondary formation mold is sectioned.
Figure 5E:
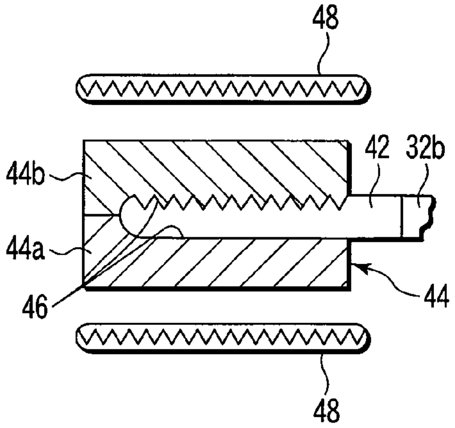
FIG. 5E is a schematic enlarged side view showing the secondary formation mold and the partial block of the distal end portion of the other end part with a small diameter of the ultrasonic transmission member shown in FIG. 5C, in a state that an outer shape of a casting cavity of the secondary formation mold has been transferred to the partial block of the distal end portion of the other end part with a small diameter of the ultrasonic transmission member by the casting cavity of the secondary formation mold and only the secondary formation mold is sectioned.

In the method for forming an ultrasonic transmission member according to this embodiment, in order to form the predetermined area 42, connected to the distal end of the other end part 32*b* with a small diameter of the ultrasonic transmission member main body 32 by the anchor structure 32*d*, in a desired outer shape, a sub-formation mold 44 having a casting cavity 46 corresponding to the desired outer shape is also prepared, as shown in FIGS. 5C to 5E.

In this embodiment, the sub-formation mold 44 is a laterally divided type having divided surfaces spreading in a vertical direction, and is formed with a metal having a high thermal conductivity, such as copper. Two half lateral pieces 44*a* and 44*b* of the sub-formation mold 44 are supported by a known opening and closing mechanism (not shown) so as to be joinable and separable. The casting cavity 46 is formed in the divided surfaces of the half lateral pieces 44*a*, 44*b* in a vertically divided manner. Heaters 48 are disposed in the sub-formation mold 44 and/or around the sub-formation mold 44.

When the half lateral pieces 44*a* and 44*b* of the sub-formation mold 44 are separated from each other and the predetermined area 42 connected to the distal end of the other end part 32*b* with a small diameter of the ultrasonic transmission member main body 32 is placed into the casting cavity 46 of the sub-formation mold 44 as shown in FIG. 5D, the predetermined area 42 is heated by the heaters 48 to a temperature in the supercooled liquid region (glass transition zone) of the metallic glass forming the predetermined area 42 and the temperature is maintained before the half lateral pieces 44*a* and 44*b* of the sub-formation mold 44 are closed.

Next, the half lateral pieces 44*a* and 44*b* of the sub-formation mold 44 are closed, the casting cavity 46 of the sub-formation mold 44 is pressed onto the metallic glass of the predetermined area 42 maintained in the temperature of the supercooled liquid region (glass transition zone) as shown in FIG. 5E, and a desired final shape of the casting cavity 46 of the sub-formation mold 44 is transferred to the metallic glass of the predetermined area 42.

Thereafter, after activation of the heaters 48 is stopped and the temperature of the metallic glass of the predetermined area 42 drops below the glass transition temperature zone Tg, namely, to the glass solidification range, the half lateral pieces 44*a*, 44*b* of the sub-formation mold 44 are opened, and the predetermined area 42 of the distal end of the other end part 32*b* with a small diameter of the ultrasonic transmission member main body 32 is taken out from the casting cavity 46 of the sub-formation mold 44.

Thus, the ultrasonic transmission member main body 32 accompanying the predetermined area 42 transferred with the desired final shape configures a final product of an elongated ultrasonic probe having a whole shape with desired dimensions, which transmits an ultrasonic wave input from an ultrasonic generator (not shown) connected to the one end part 32*a* with a large diameter through the connection tool 32*c* up to the predetermined area 42 with the desired final shape connected to the other end part 32*b* with a small diameter.

An ultrasonic wave with a predetermined frequency is input from the ultrasonic generator (not shown) connected to the connection tool 32*c* into the one end part 32*a* with a large diameter of the ultrasonic transmission member main body 32 configuring the major part of the final product of the ultrasonic probe, and it is preferable that a length L from an end surface of the one end part 32*a* with a large diameter on a side opposite to the other end part 32*b* with a small diameter to a terminal end of the predetermined area 42 with the desired final shape connected to the other end part 32*b* with a small diameter and configuring the remaining part of the final product of the ultrasonic probe is integer times of a half ($\lambda/2$) of one wavelength $\lambda$ of the ultrasonic wave. Such an elongated ultrasonic probe is used in an endoscopic operation, for example.

Further, it is also preferable that an end (namely, a starting position of transition from the one end part 32*a* with a large diameter to the other end part 32*b* with a small diameter on the outer peripheral surface of the ultrasonic transmission member main body 32) of the one end part 32*a* with a large diameter of the ultrasonic transmission member main body 32 positioned on a side of the other end part 32*b* with a small diameter substantially coincides with a node of ultrasonic wave input into the one end part 32*a* of the ultrasonic transmission member main body 32 from the ultrasonic generator (not shown) connected to the connection tool 32*c*.

As described above, while the predetermined area 42 which has been transferred with the outer shape of the casting cavity 46 of the sub-formation mold 44 is heated up to a temperature in the supercooled liquid region (glass transition zone) again and the temperature is maintained, the predetermined area 42 can be transformed to another desired shape corresponding to an outer shape of another predetermined casting cavity of another sub-formation mold by using the other sub-formation mold having the predetermined casting cavity corresponding to the other desired shape.

Third Embodiment

Next, a method for forming an ultrasonic transmission member according to a third embodiment of the present invention will be explained with reference to FIGS. 6A and 6B.

Figure 6A:
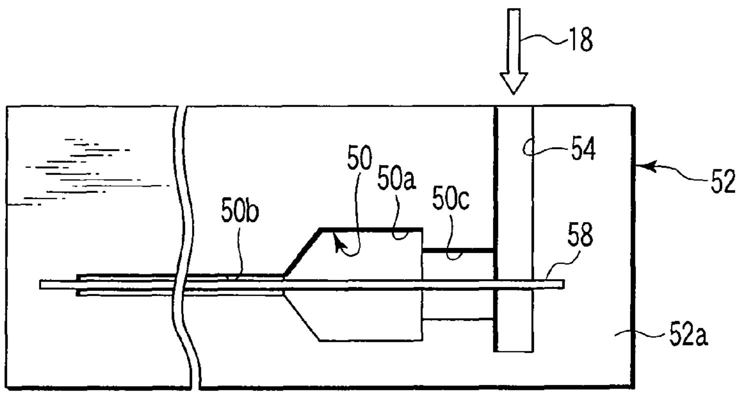
FIG. 6A is a side view schematically showing a half lateral piece of a main mold used for a method for forming an ultrasonic transmission member according to a third embodiment of the present invention, and an elongated core member disposed in a half casting cavity formed in the half lateral piece.

As shown in FIG. 6A, a main mold 52 having a casting cavity 50 is prepared. The main mold 52 also has a melted material inflow passage (runner channel) 54 to communicate the casting cavity 50 with the outer space. The casting cavity 50 has a shape corresponding to a whole outer shape and outer dimensions of a desired ultrasonic transmission member 56 whose vertical section is shown in FIG. 6B.

In this embodiment, the desired ultrasonic transmission member 56 has one end part 56*a* with a large diameter and another end part 56*b* with a small diameter, and configures an elongated ultrasonic probe transmitting an ultrasonic wave input into the one end part 56*a* up to the other end part 56*b*. A connection tool 56*c* for connecting the ultrasonic transmission member 56 to an ultrasonic generator (not shown) is formed on a side of the one end part 56*a* with a large diameter opposite to the other end part 56*b*. In this embodiment, the connection tool 56*c* is a male screw.

An ultrasonic wave with a predetermined frequency is input from the ultrasonic generator (not shown) connected to the connection tool 56*c* into the one end part 56*a* with a large diameter of the ultrasonic transmission member 56 configuring the ultrasonic probe, and it is preferable that a length L from an end surface of the one end part 56*a* with a large diameter on a side opposite to the other end part 56*b* with a small diameter to a terminal end of the other end part 56*b* with a small diameter is integer times of a half ($\lambda/2$) of one wavelength $\lambda$ of the ultrasonic wave. Such an ultrasonic transmission member 56 is used in an endoscopic operation, for example.

It is also preferable that an end of the one end part 56*a* with a large diameter of the ultrasonic transmission member 56 on a side of the other end part 56*b* with a small diameter (namely, a starting position of transition from the one end part 56*a* with a large diameter to the other end part 56*b* with a small diameter on the outer peripheral surface of the ultrasonic transmission member main body 56) substantially coincides with a node of the ultrasonic wave input into the one end part 56*a* of the ultrasonic transmission member 56 from the ultrasonic generator (not shown) connected to the connection tool 56*c*.

The casting cavity 50 of the embodiment includes one end part corresponding portion 50*a* corresponding to the one end part 56*a* with a large diameter of the ultrasonic transmission member 56, the other end part corresponding portion 50*b* corresponding to the other end part 56*b* with a small diameter of the ultrasonic transmission member 56, and a connection tool corresponding portion 50*c* corresponding to an outer shape of the connection tool 56*c* of the ultrasonic transmission member 56, and an inner end of the melted material inflow passage (runner channel) 54 is connected to a side of the connection tool corresponding portion 50*c* opposite to the one end part corresponding portion 50*a*.

The main mold 52 is a laterally divided type having divided surfaces spreading in a vertical direction and is formed with a metal having a high thermal conductivity, such as copper. Two half lateral pieces 52*a* of the main mold 52 are fixed to each other in a separable manner by a known separable fixing structure, for example, combinations of bolts and nuts. The two half lateral pieces 52*a* are symmetrical to each other, and only one of the two half lateral pieces 52*a* is shown in FIG. 6A. The casting cavity 50 and the melted material inflow passage (runner channel) 54 are formed in the divided surfaces of the two half lateral pieces 52*a* of the main mold 52 in a vertically partitioned manner.

An elongated core member 58 is disposed in the casting cavity 50 of the main mold 52 so as to extend therein from one end portion of the casting cavity 50 up to the other end potion thereof (in this embodiment, from an area of the connection tool corresponding portion 50*c* on a side opposite to the one end part corresponding portion 50*a* up to an area of the other end corresponding portion 50*b* on a side opposite to the one end part corresponding portion 50*a*). The core member 58 is formed independently from the main mold 52.

The melted alloy 18 which is the material of the metallic glass is poured into the outer end (pouring gate) of the melted material inflow passage (runner channel) 54. The melted alloy 18 can be poured into the outer end (pouring gate) of the melted material inflow passage (runner channel) 54 by the gravity or by utilizing the melted metal pressurizing-injecting mechanism 24 used in the method for forming an ultrasonic transmission member according to the second modification of the first embodiment of the present invention described with reference to FIGS. 3A and 3B.

Various known heat-radiating and/or cooling structures (not shown) are applied to the main mold 52 such that the melted alloy 18 which is the material of the metallic glass and which has been poured into the casting cavity 50 through the melted material inflow passage (runner channel) 54 is solidified in a liquid phase state thereof. As a result, the melted alloy 18 which has been poured into the casting cavity 50 is rapidly cooled at a cooling rate of 10 K/sec or more. The melted alloy 18 which has been poured into the casting cavity 50 is cooled in this manner to be changed to an amorphous alloy (so-called "metallic glass") where no crystalline grain boundary is present, so that a shape and dimensions of the casting cavity 50 are transferred to the amorphous alloy (so-called "metallic glass") precisely.

The ultrasonic transmission member 56 formed with the metallic glass, which has been in a glass solidification range in the casting cavity 50 and which has been transferred with a shape of the casting cavity 50, and accompanying the core member 58 is taken out from the main mold 52 after further heat radiation for a predetermined time period. At this time, the ultrasonic transmission member 56 shown by a solid line in FIG. 6B includes a melted material inflow passage corresponding portion 54*a* with a shape corresponding to the melted material inflow passage (runner channel) 54 at the connection tool 56*c* as shown by a two-dots chain line in FIG. 6B.

Next, the core member 58 is withdrawn from the ultrasonic transmission member 56 and the melted material inflow passage corresponding portion 54*a* is removed from the connection tool 56*c* by machining.

As a result, the ultrasonic transmission member 56 having an elongated center hole, which corresponds to the core member 58 and which coaxially extends from the outer end of the connection tool 56*c* to the outer end of the other end part 56*b* with a small diameter, can be obtained.

In this embodiment, the connection tool corresponding portion 50*c* is interposed between the one end part corresponding portion 50*a* with a large diameter and the inner end of the melted material inflow passage (runner channel) 54 in the casting cavity 50 of the main mold 52. But, it is possible to remove the connection tool corresponding portion 50*c* and to connect the inner end of the melted material inflow passage (runner channel) 54 directly to an end of the one end part corresponding portion 50*a* with a large diameter on a side opposite to the other end part corresponding portion 50*b* with a small diameter, like in the casting cavity 12 of the main mold 10 of the first embodiment described with reference to FIGS. 1A to 1C.

In this case, after the ultrasonic transmission member 56 is taken out from the casting cavity 50 of the main mold 52 and the core member 58 is withdrawn from the ultrasonic transmission member 56, it is necessary to form a connection tool 56*c* by machining the melted material inflow passage corresponding portion 54*a*, like the case in which the ultrasonic transmission member 16 is formed by the casting cavity 12 of the main mold 10 of the first embodiment described with reference to FIGS. 1A to 1C. And, during this machining work, various known cooling actions, such as application of a cooling medium including a cooling liquid, must be applied not to reach a temperature of the metallic glass of the melted material inflow passage corresponding portion 54*a* to the crystallization temperature thereof or higher (that is, the metallic glass keeps amorphous and is not crystallized).

Modification of Third Embodiment

Figure 7A:
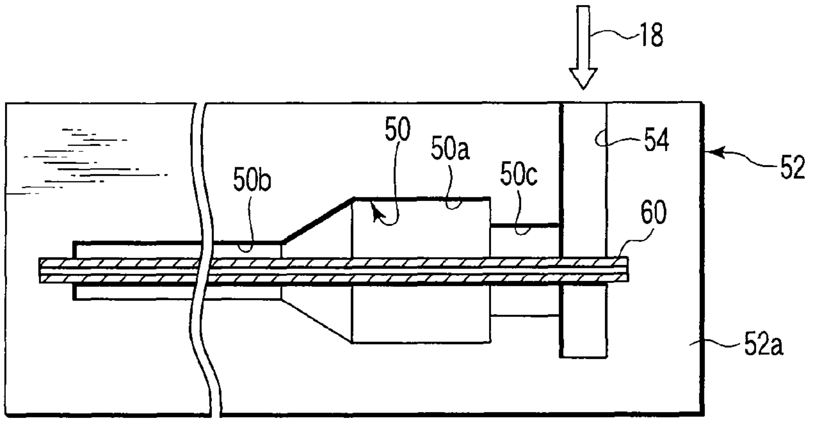
FIG. 7A is a side view schematically showing a half lateral piece of a main mold used for a modification of the method for forming an ultrasonic transmission member according to the third embodiment of the present invention, and an elongated hollow member disposed in a half casting cavity formed in the half lateral piece.

Next, a modification of the method for forming an ultrasonic transmission member according to the third embodiment of the present invention will be explained with reference to FIGS. 7A and 7B.

Figure 6B:
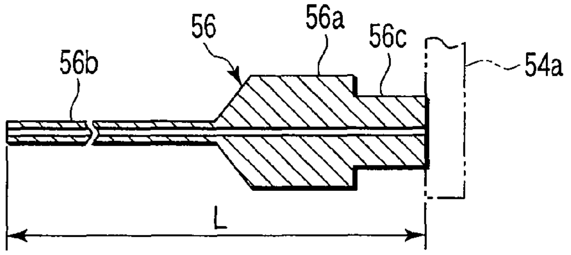
FIG. 6B is a schematic vertical sectional view of an ultrasonic transmission member formed with metallic glass by using the casting cavity of the main mold with the elongated core member shown in FIG. 6A.

A difference of the modification from the method for forming an ultrasonic transmission member according to the third embodiment of the present invention described with reference to FIGS. 6A and 6B is that an elongated hollow member 60 is disposed in the casting cavity 50 of the main mold 52 instead of the elongated core member 58. The hollow member 60 is formed independently from the main mold 52.

After the ultrasonic transmission member 56 is taken out from the casting cavity 50 of the main mold 52, the elongated hollow member 60 is not withdrawn out from the ultrasonic transmission member 56.

Figure 7B:
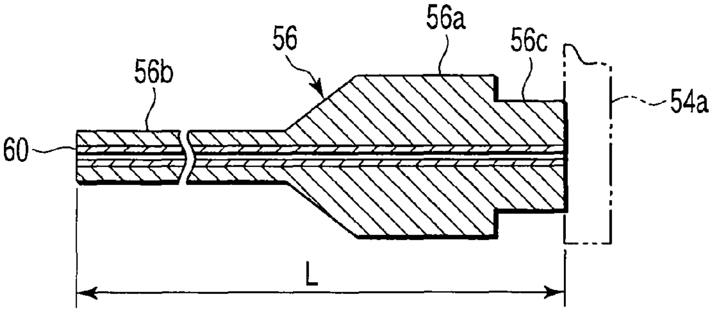
FIG. 7B is a schematic vertical sectional view of an ultrasonic transmission member formed with metallic glass by using the casting cavity of the main mold with the elongated hollow member shown in FIG. 7A.

When the melted material inflow passage corresponding portion 14*a* shown by a two-dots chain line in FIG. 7B and connected to the connection tool 56*c* is removed by machining from the ultrasonic transmission member 56 just after the ultrasonic transmission member 56 is taken out from the casting cavity 50 of the main mold 50, both end portions of the hollow member 60 projecting from the outer end of the other end part 56*b* with a small diameter of the ultrasonic transmission member 56 and the outer end of the connection tool 56*c* are also removed by machining.

As a result, the ultrasonic transmission member 56 accompanying the elongated hollow pipe 60 extending coaxially from the outer end of the connection tool 56*c* to the outer end of the other end part 56*b* with a small diameter can be obtained. Since the elongated hollow pipe 60 is used together with the ultrasonic transmission member 56, it must be formed with a material whose quality does not change even under an environment in which the ultrasonic transmission member 56 is used.

Fourth Embodiment

Next, a method for forming an ultrasonic transmission member according to a fourth embodiment of the present invention will be explained with reference to FIGS. 8A to 8C.

Figure 8A:
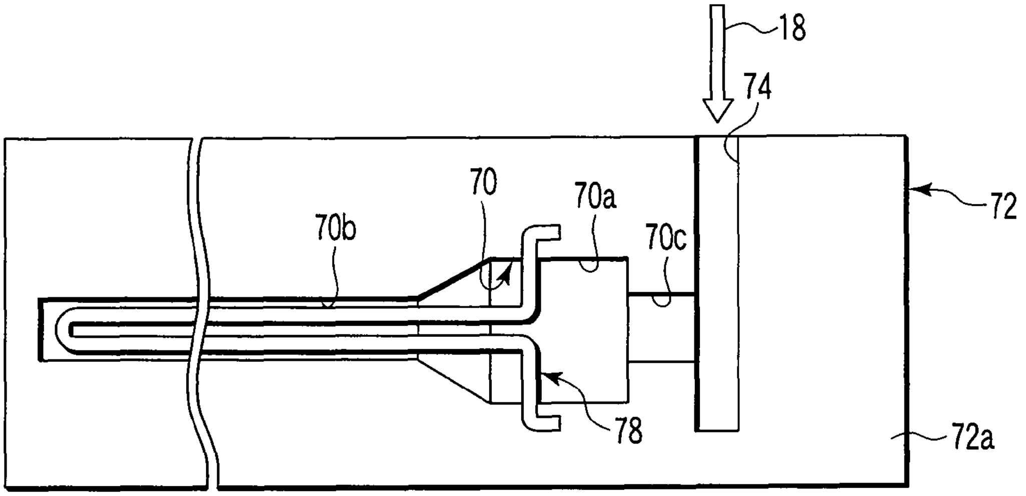
FIG. 8A is a side view schematically showing a half lateral piece of a main mold used in a method for forming an ultrasonic transmission member according to a fourth embodiment of the present invention, and an elongated U-shaped pipe disposed in a half casting cavity formed in the half lateral piece.
Figure 8B:
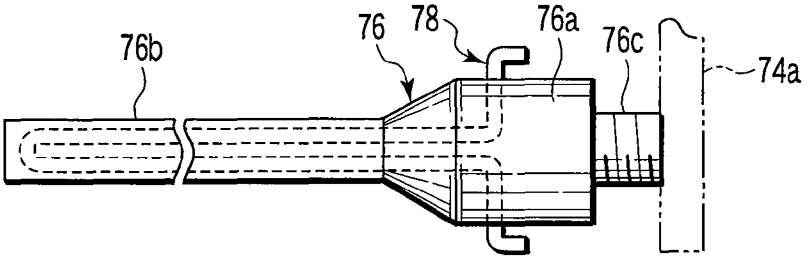
FIG. 8B is a schematic side view of an ultrasonic transmission member with the elongated U-shaped pipe shown in FIG. 8A, which has been formed with metallic glass by using the casting cavity of the main mold.

As shown in FIG. 8A, a main mold 72 having a casting cavity 70 is prepared. The main mold 72 also has a melted material inflow passage (runner channel) 74 for communicating the casting cavity 70 with the outer space. The casting cavity 70 has a shape corresponding to a whole outer shape and outer dimensions of a desired ultrasonic transmission member 76 shown in FIG. 8C.

In the embodiment, the desired ultrasonic transmission member 76 has one end part 76*a* with a large diameter and the other end part 76*b* with a small diameter, and which configures an elongated ultrasonic probe transmitting an ultrasonic wave input into the one end part 76*a* up to the other end part 76*b*. A connection tool 76*c* for connecting the ultrasonic transmission member 76 to a known ultrasonic generator USG is formed on a side of the one end part 76*a* with a large diameter opposite to the other end part 76*b*. In this embodiment, the connection tool 76*c* is a male screw. Such an ultrasonic transmission member 76 is used in an endoscopic operation, for example.

The casting cavity 70 in this embodiment includes a one end part corresponding portion 70*a* corresponding to the one end part 76*a* with a large diameter of the ultrasonic transmission member 76, an other end part corresponding portion 70*b* corresponding to the other end part 76*b* with a small diameter of the ultrasonic transmission member 76, and a connection tool corresponding portion 70*c* corresponding to an outer shape of the connection tool 76*c* of the ultrasonic transmission member 76, and an inner end of the melted material inflow passage (runner channel) 74 is connected to a side of the connection tool corresponding portion 70*c* opposite to the one end part corresponding portion 70*a*.

The main mold 72 is a laterally divided type having divided surfaces spreading in a vertical direction, and is formed of a metal with a high thermal conductivity, such as copper. Two half lateral pieces 72*a* of the main mold 72 are fixed to each other in a separable manner by a known separable fixing structure, for example, a combination of bolts and nuts. The two half lateral pieces 72*a* are symmetrical to each other, and only one of the two half lateral pieces 72*a* is shown in FIG. 8A. The casting cavity 70 and the melted material inflow passage (runner channel) 74 are formed in divided surfaces of the two half lateral pieces 72*a* of the main mold 72 in a vertically partitioned manner.

A U-shaped pipe 78 extending from the one end portion of the casting cavity 70 to the other end portion thereof (in this embodiment, from an inner peripheral surface of the one end part corresponding portion 70*a* to the vicinity of an outer end of the other end part corresponding portion 70*b* on a side opposite to the one end part corresponding portion 70*a*) and returning back to the one end portion is disposed in the casting cavity 70 of the main mold 72. Specifically, the U-shaped pipe 78 is prepared independently from the main mold 72. Both end portions of the U-shaped pipe 78 project from two positions spaced from each other on the inner peripheral surface of the one end part corresponding portion 70*a* of the main mold 72 in a radially outward direction of the one end part corresponding portion 70*a*, and a bent portion of the U-shaped pipe 78 bent 180° is positioned in the vicinity of the outer end of the other end part corresponding portion 70*b* in the casting cavity 70 of the main mold 72.

The melted alloy 18 which is the material of the metallic glass is poured into an outer end (pouring gate) of the melted material inflow passage (runner channel) 74. The melted alloy 18 can be poured into the outer end (pouring gate) of the melted material inflow passage (runner channel) 74 by the gravity or by utilizing the melted metal pressurizing-injecting mechanism 24 used in the second modification of the method for forming an ultrasonic transmission member according to the first embodiment of the present invention described with reference to FIGS. 3A and 3B.

Various known heat-radiating and/or cooling structures (not shown) are applied to the main mold 72 such that the melted alloy 18 which is the material of the metallic glass and which has been poured into the casting cavity 70 through the melted material inflow passage (runner channel) 74, is solidified in a liquid phase state. As a result, the melted alloy 18 which has been poured into the casting cavity 70 is cooled at a cooling rate of 10 K/sec or more. The melted alloy 18 which has been poured into the casting cavity 70 is cooled in this manner to be changed to an amorphous alloy (so-called "metallic glass") where no crystalline grain boundaries are present, so that a shape and dimensions of the casting cavity 70 are transferred to the amorphous alloy (so-called "metallic glass") precisely.

The metallic glass which has been in a glass solidification range and which has been transferred with the shape of the casting cavity 70 configures the ultrasonic transmission member 76, and, together with the U-shaped pipe 78, is taken out from the main mold 72 after further heat radiation for a predetermined time period. At this time, the ultrasonic transmission member 76 shown by a solid line in FIG. 6B, accompanies a melted material inflow passage corresponding portion 74*a* with a shape corresponding to the melted material inflow passage (runner channel) 74 at the connection tool 76*c*, as shown by a two-dots chain line in FIG. 8B.

Next, the melted material inflow passage corresponding portion 74*a* is removed from the connection tool 76*c* by machining.

Incidentally, the connection tool corresponding portion 70*c* is interposed between the one end part corresponding portion 70*a* with a large diameter and the inner end of the melted material inflow passage (runner channel) 74 in the casting cavity 70 of the main mold 72, but it is possible to remove the connection tool corresponding portion 70*c* and to connect the inner end of the melted material inflow passage (runner channel) 74 directly to an end of the one end part corresponding portion 70*a* with a large diameter on a side opposite to the other end part corresponding portion 70*b* with a small diameter, like the casting cavity 12 of the main mold 10 of the first embodiment described with reference to FIGS. 1A to 1C.

In this case, after the ultrasonic transmission member 76 is taken out from the casting cavity 70 of the main mold 72, it is necessary to form the connection tool 76*c* by machining the melted material inflow passage corresponding portion 74*a*, like the case that the ultrasonic transmission member 16 is formed by the casting cavity 12 of the main mold 10 of the first embodiment described with reference to FIGS. 1A to 1C. During this machining work, various known cooling actions, such as application of a cooling medium including a cooling liquid, must be applied not to reach a temperature of the metallic glass of the melted material inflow passage corresponding portion 74*a* to the crystallization temperature thereof or higher (that is, the metallic glass keeps amorphous and is not crystallized).

An ultrasonic wave with a predetermined frequency is input into the one end part 76*a* with a large diameter of the ultrasonic transmission member 76 from the ultrasonic generator USG connected to the connection tool 76*c*, but it is preferable that a length L from an end surface of the one end part 76*a* with a large diameter on a side opposite to the other end part 76*b* with a small diameter up to an outer end of the other end part 76*b* with a small diameter is integer times of a half ($\lambda/2$) of one wavelength $\lambda$ of the ultrasonic wave.

Further, it is preferable that an end of the one end part 76*a* with a large diameter of the ultrasonic transmission member 76 positioned on a side opposite to the other end part 76 with a small diameter (that is, a starting position of transition from the one end part 76*a* with a large diameter to the other end part 76*b* with a small diameter on an outer peripheral surface of the ultrasonic transmission member 76) substantially coincides with a node of the ultrasonic wave input into the one end part 76*a* of the ultrasonic transmission member 76 from the ultrasonic generator USG connected to the connection tool 76*c*.

Further, it is preferable that the both end portions of the U-shaped pipe 78 projecting from the outer peripheral surface of the one end part 76*a* with a large diameter of the ultrasonic transmission member 76 are positioned at the node of the ultrasonic wave input from the ultrasonic generator USG into the one end part 76*a* of the ultrasonic transmission member 76.

Thereby, it is possible to considerably reduce the possibility that the both end portions of the U-shaped pipe 78 are damaged by vibrations of the ultrasonic wave input from the ultrasonic generator USG into the one end part 76*a* of the ultrasonic transmission member 76.

Figure 8C:
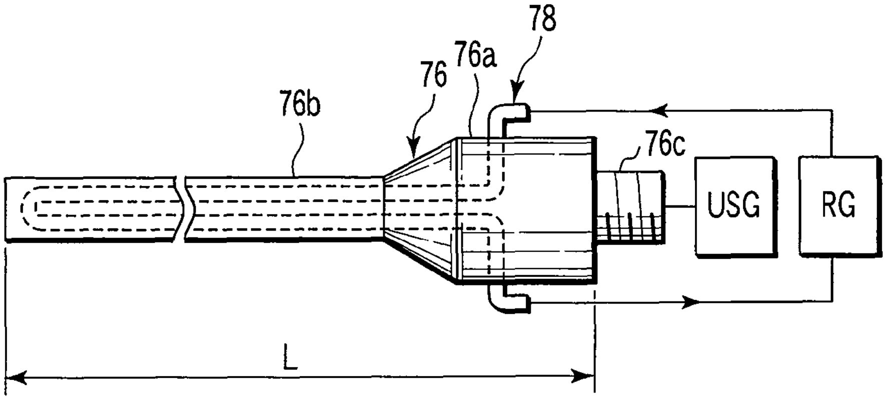
FIG. 8C is a schematic side view of one example for using the ultrasonic transmission member with the U-shaped pipe shown in FIG. 8B.

As shown in FIG. 8C, the both end portions of the U-shaped pipe 78 of the ultrasonic transmission member 76 are connected to a known cooling apparatus RG. The cooling apparatus RG supplies, for example, a cooling medium including a liquid to the one end portion of the U-shaped pipe 78 so that the cooling medium passing through the U-shaped pipe 78 absorbs heat generated when the ultrasonic transmission member 76 transmits the ultrasonic wave and is collected to the cooling apparatus RG through the other end portion of the U-shaped pipe 78. The cooling apparatus RG radiates the collected heat contained in the cooling medium and supplies the cooling medium after heat radiation to the one end portion of the U-shaped pipe 78 again.

Fifth Embodiment

Next, a method for forming an ultrasonic transmission member according to a fifth embodiment of the present invention will be explained with reference to FIGS. 9A to 9E.

Figure 9B:
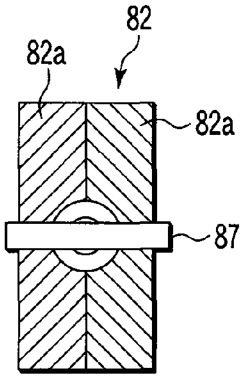
FIG. 9B is a schematic sectional view of the mold shown in FIG. 9A, taken along a line IXB-IXB in FIG. 9A.
Figure 9A:
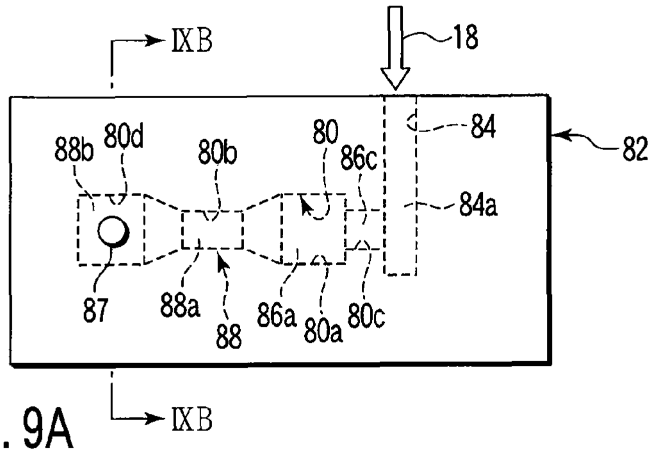
FIG. 9A is a side view schematically showing a side surface of a mold used for a method for forming an ultrasonic transmission member according to a fifth embodiment of the present invention.
Figure 9C:
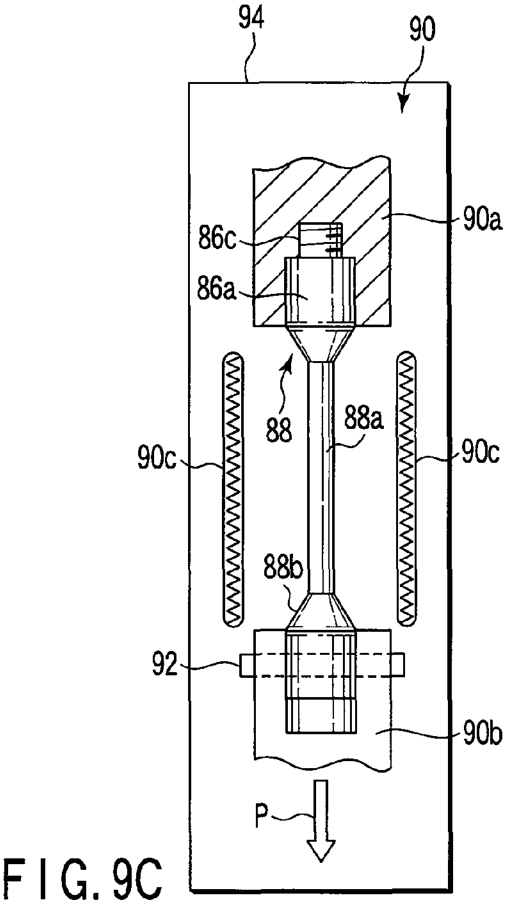
FIG. 9C is a side view schematically showing a state in which both end parts of an ultrasonic transmission member block formed with metallic glass by using a casting cavity of the mold shown in FIG. 9A are fixed to a pulling apparatus and the ultrasonic transmission member block is being pulled by the pulling apparatus while an intermediate portion corresponding area is being heated up to a supercooled liquid region of the metallic glass, and a part of the pulling apparatus is sectioned.
Figure 9D:
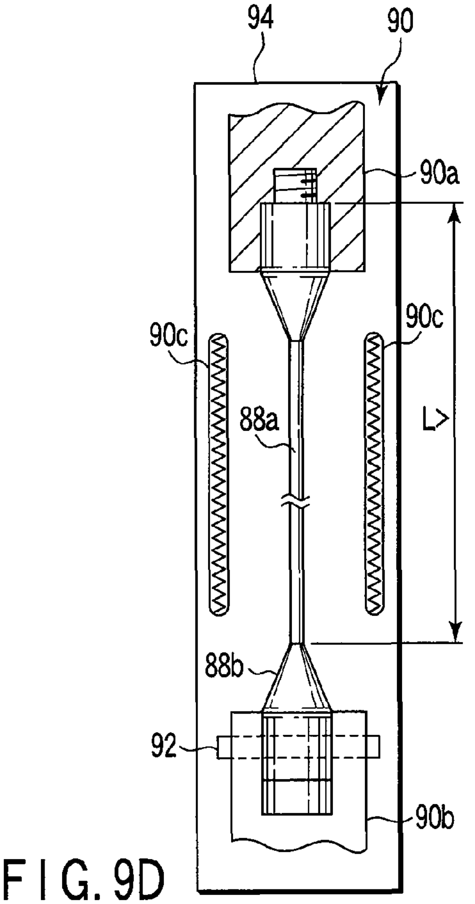
FIG. 9D is a side view schematically showing a state in which the ultrasonic transmission member block has been pulled up to a predetermined length or more by the pulling apparatus in FIG. 9C.

As shown in FIG. 9A, a mold 82 having a casting cavity 80 is prepared. The mold 82 also has a melted material inflow passage (runner channel) 84 for communicating the casting cavity 80 with the outer space. The casting cavity 80 has a shape corresponding to a whole outer shape of a desired ultrasonic transmission member 86 shown in FIG. 9E except for a length of the desired ultrasonic transmission member 86.

In this embodiment, the desired ultrasonic transmission member 86 has one end part 86*a* with a large diameter and the other end part 86*b* with a small diameter, and configures an elongated flexible ultrasonic probe having a predetermined length L and transmitting an ultrasonic wave input into the one end part 86*a* up to the other end part 86*b*. A connection tool 86*c* for connecting the ultrasonic transmission member 86 to an ultrasonic generator (not shown) is formed on a side of the one end part 86*a* with a large diameter opposite to the other end part 86*b*. In this embodiment, the connection tool 86*c* is a male screw. Such an ultrasonic transmission member 86 is used to remove plaque within a blood vessel in an operation using a catheter, for example.

An ultrasonic wave with a predetermined frequency is input into the one end part 86*a* of the ultrasonic transmission member 86 from the ultrasonic generator (not shown) connected to the connection tool 86*c*, but it is preferable that a length L from an end surface of the one end part 86*a* with a large diameter positioned on a side opposite to the other end part 86*b* to a terminal end of the other end part 86*b* is integer times of a half (λ/2) of one wavelength λ of the ultrasonic wave.

Further, it is preferable that an end of the one end part 86*a* with a large diameter of the ultrasonic transmission member 86 positioned on a side opposite to the other end part 86*b* with a small diameter (that is, a starting position of transition from the one end part 86*a* with a large diameter to the other end part 86*b* with a small diameter on an outer peripheral surface of the ultrasonic transmission member 86) substantially coincides with a node of the ultrasonic wave input into the one end part 86*a* of the ultrasonic transmission member 86 from the ultrasonic generator (not shown) connected to the connection tool 86*c*.

The casting cavity 80 in the embodiment includes one end part corresponding portion 80*a* corresponding to the one end part 86*a* with a large diameter of the ultrasonic transmission member 86, an intermediate portion 80*b* extending from one end of the one end part corresponding portion 80*a* concentrically and being thicker and shorter than the other end part 86*b* with a small diameter of the ultrasonic transmission member 86, a connection tool corresponding portion 80*c* extending from the other end of the one end part corresponding portion 80*a* concentrically and corresponding to an outer shape of the connection tool 86*c* of the ultrasonic transmission member 86, and an other end portion 80*d* positioned on a side of the intermediate portion 80*b* opposite to the one end part corresponding portion 80*a*. And, an inner end of a melted material inflow passage (runner channel) 84 is connected to a side of the connection tool corresponding portion 80*c* opposite to the one end part corresponding portion 80*a*. A straight core 87 penetrates the other end portion 80*d* of the casting cavity 80 in a direction intersecting a longitudinal direction of the casting cavity 80.

As shown in FIG. 9B, the mold 82 is a laterally-divided type having divided surfaces spreading in a vertical direction and is formed with a metal having a high thermal conductivity, such as copper. Two half lateral pieces 82*a* of the mold 82 are fixed to each other in a separable manner by a known separable fixing structure, for example, a combination of bolts and nuts. The two half lateral pieces 82*a* are symmetrical to each other, and the casting cavity 80 and the melted material inflow passage (runner channel) 84 are formed in the divided surfaces of the two half lateral pieces 82*a* of the mold 82 in a vertically partitioned manner.

The melted alloy 18 which is the material of the metallic glass is poured into an outer end (pouring gate) of the melted material inflow passage (runner channel) 84. The melted alloy 18 can be poured into the outer end (pouring gate) of the melted material inflow passage (runner channel) 58 by gravity or by utilizing the melted metal pressurizing-injecting mechanism 24 used in the method for forming an ultrasonic transmission member according to the second modification of the first embodiment of the present invention described with reference to FIGS. 3A and 3B.

Various known heat-radiating and/or cooling structures (not shown) are applied to the mold 82 such that the melted alloy 18 which is the material of the metallic glass and which has been poured into the casting cavity 80 through the melted material inflow passage (runner channel) 84, is solidified in a liquid phase state. As a result, the melted alloy 18 which has been poured into the casting cavity 70 is cooled at a cooling rate of 10 K/sec or more. The melted alloy 18 which has been poured into the casting cavity 70 is cooled in this manner to be changed to an amorphous alloy (so-called "metallic glass") where no crystalline grain boundaries are present, so that a shape and dimensions of the casting cavity 80 are transferred to the amorphous alloy (so-called "metallic glass") precisely.

Figure 9E:
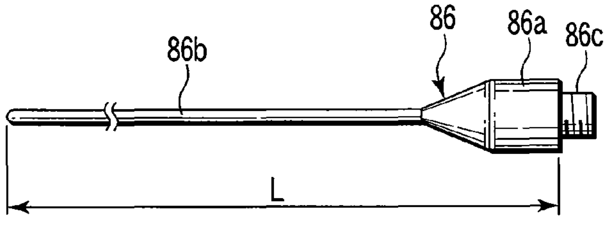
FIG. 9E is a schematic side view of an ultrasonic transmission member which has been finally formed by the method for forming an ultrasonic transmission member according to the fifth embodiment of the present invention, the method including various steps shown in FIGS. 9A to 9D.

Metallic glass which has been in a glass solidification range in the casting cavity 80 and which has been transferred with the shape of the casting cavity 80 configures an ultrasonic transmission member block 88 corresponding to a whole outer shape of the ultrasonic transmission member 86 shown in FIG. 9E except that its length is less than the predetermined length L.

The ultrasonic transmission member block 88 includes one end part 86*a* with a large diameter transferred with a shape and dimensions of the one end part corresponding portion 80*a* of the casting cavity 80 and being equal to the one end part 86*a* with a large diameter of the ultrasonic transmission member 86, a connection tool 86*c* transferred with a shape and dimensions of the connection tool corresponding portion 80*c* of the casting cavity 80 and being equal to the connection tool 86*c* of the ultrasonic transmission member 86, a melted material inflow passage corresponding portion 84*a* transferred with a shape and dimensions of the melted material inflow passage (runner channel) 84 of the casting cavity 80, an intermediate portion corresponding part 88*a* transferred with a shape and dimensions of the intermediate portion 80*b* of the casting cavity 80, and an other end part 88*b* transferred with a shape and dimensions of the other end portion 80*d* of the casting cavity 80.

After heat radiation for a predetermined time, the core 87 is removed and the ultrasonic transmission member block 88 is taken out from the mold 82.

Next, the melted material inflow passage corresponding portion 84*a* is removed from the connection tool 86*c* by machining.

Incidentally, the connection tool corresponding portion 80*c* is interposed between the one end part corresponding portion 80*a* with a large diameter and the inner end of the melted material inflow passage (runner channel) 84 in the casting cavity 80 of the mold 82, but it is possible to remove the connection tool corresponding portion 80*c* and to connect the inner end of the melted material inflow passage (runner channel) 84 directly to an end of the one end part corresponding portion 80*a* with a large diameter on a side opposite to the intermediate portion 80*b*, like the casting cavity 12 of the main mold 10 of the first embodiment described with reference to FIGS. 1A to 1C.

In this case, after the ultrasonic transmission member block 88 is taken out from the casting cavity 80 of the mold 82, it is necessary to form the connection tool 86*c* by machining the melted material inflow passage corresponding portion 84*a*, like the case that the ultrasonic transmission member 16 is formed by the casting cavity 12 of the main mold 10 of the first embodiment described with reference to FIGS. 1A to 1C. During this machining work, various known cooling actions, such as application of a cooling medium including a cooling liquid, must be applied not to reach a temperature of the metallic glass of the melted material inflow passage corresponding portion 84*a* to the crystallization temperature thereof or higher (that is, the metallic glass keeps amorphous and is not crystallized).

After the ultrasonic transmission member block 88 is taken out from the casting cavity 80 of the mold 82 as described above and further the melted material inflow passage corresponding portion 84*a* is removed from the connection tool 86*c* or the connection tool 86*c* is formed from the melted material inflow passage corresponding portion 84*a* by machining, the ultrasonic transmission member block 88 is set to a pulling apparatus 90 for pulling the ultrasonic transmission member block 88 to a predetermined length while the intermediate portion corresponding part 88*a* is heated to a supercooled liquid region (glass transition zone) and the temperature thereof is maintained in the supercooled liquid region (glass transition zone).

The pulling apparatus 90 includes a fixing stand 90*a* on which the connection tool 86*c* of the ultrasonic transmission member block 88 is detachably fixed, a pulling movement stand 90*b* on which the other end portion corresponding part 88*b* of the ultrasonic transmission member block 88 is detachably fixed, and heaters 90*c* which surround the intermediate portion corresponding part 88*b* of the ultrasonic transmission member block 88 while the connection tool 86*c* of the ultrasonic transmission member block 88 is detachably fixed on the fixing stand 90*a* and the other end portion corresponding part 88*b* is detachably fixed on the pulling movement stand 90*b*.

A pulling rod 92 is inserted into a through-hole in the other end portion corresponding part 88*b* of the ultrasonic transmission member block 88 after the core 87 has been removed through a through-hole formed in the pulling movement stand 90*b* to cross the other end portion corresponding part 88*b* of the ultrasonic transmission member block 88 in a direction orthogonal to a longitudinal direction of the ultrasonic transmission member block 88, and both end portions of the pulling rod 92 are supported in the through-hole of the pulling movement stand 90*b*.

Accordingly, in the pulling apparatus 90, the other end portion corresponding part 88*b* of the ultrasonic transmission member block 88 is pulled in the longitudinal direction of the ultrasonic transmission member block 88 by the pulling movement stand 90*b* through the pulling rod 92, as shown by an arrow P, while the heaters 90*c* heat the intermediate portion corresponding part 88*a* of the ultrasonic transmission member block 88 to the supercooled liquid region (glass transition zone) and the temperature thereof is maintained in the supercooled liquid region (glass transition zone), so that the intermediate portion corresponding part 88*a* can be thinned.

Pulling of the other end portion corresponding part 88*b* of the ultrasonic transmission member block 88 by the pulling movement stand 90*b* is stopped when the length from the end of the one end part 86*a* of the ultrasonic transmission member block 88 on the side of the connection tool 86*c* to an end of the intermediate portion corresponding part 88*a* of the ultrasonic transmission member block 88 on a side of the other end portion corresponding part 88*b* reaches the abovementioned predetermined distance L or more. At this time, it is preferable that an outer diameter of the intermediate portion corresponding part 88*a* is a dimension which can perform a flexibility that a plastic deformation does not occur even if the intermediate portion corresponding part 88*a* is bent 90° or more and the intermediate portion corresponding part 88*a* returns back to the original straight state elastically after a force applied to the intermediate portion corresponding part 88*a* to bend it is removed. For example, it is preferable that the outer diameter is in a range of about 0.2 mm to about 1 mm.

It is preferable that the abovementioned heating to the intermediate portion corresponding part 88*a* of the ultrasonic transmission member block 88 by the heaters 90*c* and the abovementioned pulling by the pulling movement stand 90*b* are carried out while the pulling apparatus 90 is surrounded by a container 94 and an inner space of the container 94 is vacuumed or charged with an inert gas.

By performing the heating in the vacuum or inert gas, the heated intermediate portion corresponding part 88*a* is prevented from being adversely affected (for example, oxidized) by the oxygen in the air.

After the pulling and the heating are stopped and the temperature of the heated and pulled intermediate portion corresponding part 88*a* drops below the supercooled liquid region, the ultrasonic transmission member block 88 is taken out from the pulling apparatus 90.

Thereafter, the end of the intermediate portion corresponding part 88*a* of the ultrasonic transmission member block 88 positioned on the side of the other end portion corresponding part 88*b* is cut off such that the distance from the end of the one end part 86*a* of the ultrasonic transmission member block 88 on the side of the connection tool 86*c* to the end of the intermediate portion corresponding part 88*a* of the ultrasonic transmission member block 88 on the side of the other end portion corresponding part 88*b* is the abovementioned predetermined distance L.

As a result, the ultrasonic transmission member block 88 becomes the ultrasonic transmission member 86 shown in FIG. 9E.

Sixth Embodiment

Next, a method for forming an ultrasonic transmission member according to a sixth embodiment of the present invention will be explained with reference to FIGS. 10A to 10C.

Figure 10A:
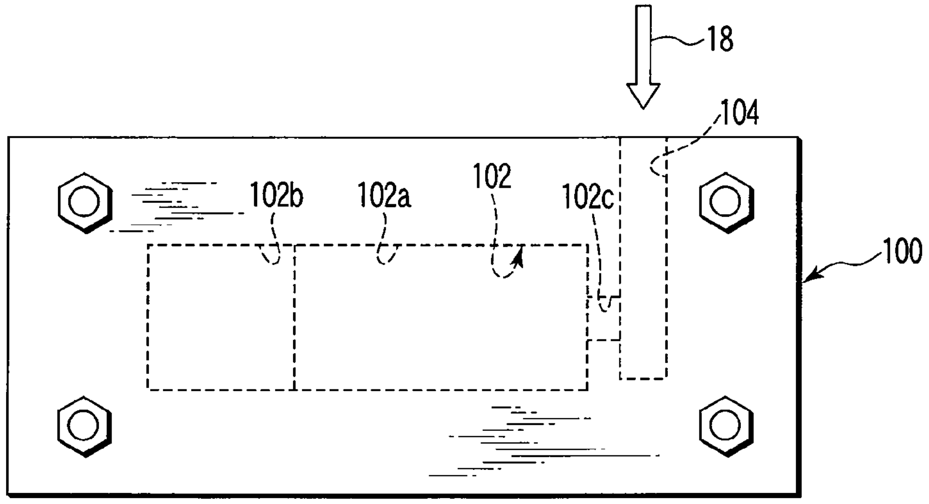
FIG. 10A is a schematic side view of a main mold used for a method for forming an ultrasonic transmission member according to a sixth embodiment of the present invention.
Figure 10B:
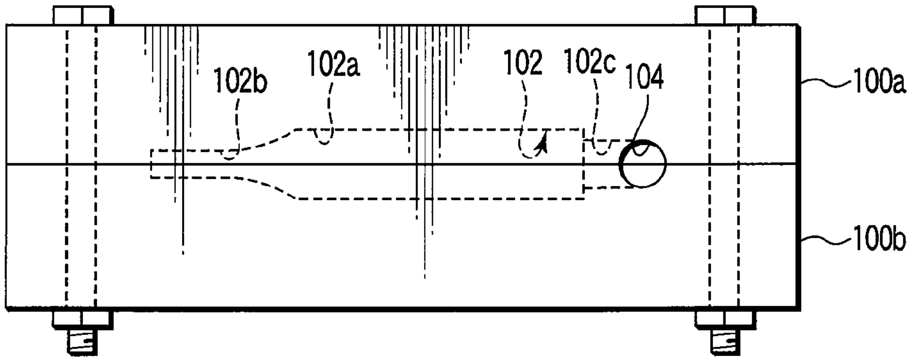
FIG. 10B is a schematic top view of the main mold shown in FIG. 10A.

As shown in FIGS. 10A and 10B, a main mold 100 having a casting cavity 102 is prepared. The main mold 100 also has a melted material inflow passage (runner channel) 104 for communicating the casting cavity 102 with the outer space. The casting cavity 102 has a whole outer shape and outer dimensions of a desired ultrasonic transmission member 106 shown in FIG. 10C.

In this embodiment, the desired ultrasonic transmission member 106 has one end part 106*a* with a large rectangular shape and another end part 106*b* with a small rectangular shape. An end portion of the other end part 106*b* positioned on a side of the one end part 106*a* gradually increases in thickness and is finally connect with an end of the one end part 106*a* positioned adjacent to the other end part 106*b*. That is, the other end part 106*b* has a substantially wedge shape as a whole. Such an ultrasonic transmission member 106 configures an ultrasonic horn transmitting an ultrasonic wave input into the one end part 106*a* up to the other end part 106*b*. Such an ultrasonic horn is used for welding utilizing an ultrasonic wave, for example.

A connection tool 106*c* for connecting the ultrasonic transmission member 106 to an ultrasonic generator (not shown) is formed on a side of the large one end part 106*a* opposite to the small other end part 106*b*. In this embodiment, the connection tool 106*c* is a male screw.

An ultrasonic wave with a predetermined frequency is input into the one end part 106*a* of the ultrasonic transmission member 106 from the ultrasonic generator (not shown) connected to the connection tool 106*c*, and it is preferable that a length L from an end surface of the large one end part 106*a* on the side opposite to the small other end part 106*b* to a terminal end of the other end part 106*b* is integer times of a half (λ/2) of one wavelength λ of the ultrasonic wave. Such an ultrasonic transmission member 106 is used in an ultrasonic (high frequency) welding machine.

Further, it is preferable that an end of the large one end part 106*a* of the ultrasonic transmission member 106 on the side of the small other end part 106*b* (that is, a starting position of transition from the large one end part 106*a* to the small other end part 106*b* on an outer peripheral surface of the ultrasonic transmission member 106) substantially coincides with a node of the ultrasonic wave input into the one end part 106*a* of the ultrasonic transmission member 106 from the ultrasonic generator (not shown) connected to the connection tool 106*c*.

The casting cavity 102 in the embodiment includes a one end part corresponding portion 102*a* corresponding to the large one end part 106*a* of the ultrasonic transmission member 106, an other end part corresponding portion 102*b* corresponding to the small other end part 106*b* of the ultrasonic transmission member 106, and a connection tool corresponding portion 102*c* corresponding to the connection tool 106*c* of the ultrasonic transmission member 106.

The main mold 100 is a laterally-divided type having divided surfaces spreading in a vertical direction, and is formed from a metal having a high thermal conductivity, such as copper. Two half lateral pieces 100*a* and 100*b* the main mold 100 are symmetrical to each other and are fixed to each other in a separable manner by a known separable fixing structure, for example, a combination of bolts and nuts. The casting cavity 102 and the melted material inflow passage (runner channel) 104 are formed in the divided surfaces of the two half lateral pieces 100*a* and 100*b* of the main mold 100 in a vertically partitioned manner.

The melted material inflow passage (runner channel) 104 has an outer end (pouring gate) opened in an upper surface of the main mold 100 and an inner end connected to a predetermined area of the casting cavity 102, in this embodiment to a side of the connection tool corresponding portion 102*c* opposite to the one end part corresponding portion 102*a*.

The melted alloy 18 which is the material of the metallic glass is poured into the outer end (pouring gate) of the melted material inflow passage (runner channel) 104. The melted alloy 18 can be poured into the outer end (pouring gate) of the melted material inflow passage (runner channel) 104 by the gravity or by utilizing the melted metal pressurizing-injecting mechanism 24 used in the second modification of the method for forming an ultrasonic transmission member according to the first embodiment of the present invention described with reference to FIGS. 3A and 3B.

Various known heat-radiating and/or cooling structures (not shown) are applied to the main mold 100 to solidify the melted alloy 18, which is the material of the metallic glass and which has been poured into the casting cavity 102 through the melted material inflow passage (runner channel) 104, in a liquid phase state. As a result, the melted alloy 18 which has been poured into the casting cavity 102 is cooled at a cooling rate of 10 K/sec or more. The melted alloy 18 which has been poured into the casting cavity 102 is rapidly cooled in this manner, so that a shape and dimensions of the casting cavity 102 are transferred to the amorphous alloy (so-called "metallic glass") precisely.

The ultrasonic transmission member 106 formed with the metallic glass, which has been in a glass solidification range in the casting cavity 102 and which has been transferred with the shape of the casting cavity 102, is taken out from the main mold 100 after further heat radiation for a predetermined time period. At this time, a side of the connection tool 106*c* opposite to the large one end part 106*a* accompanies a melted material inflow passage corresponding portion (not shown) having a shape corresponding to the melted material inflow passage (running channel) 104.

Figure 10C:
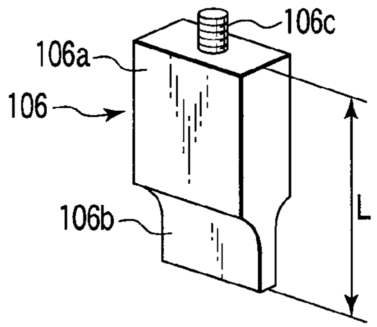
FIG. 10C is a schematic side view of an ultrasonic transmission member formed with metallic glass by using the main mold schematically shown in FIGS. 10A and 10B.

Accordingly, the melted material inflow passage corresponding portion (not shown) is finally removed from the connection tool 106*c* by machining, so that the ultrasonic transmission member 106 serving as an ultrasonic horn shown in FIG. 10C is completed.

Incidentally, the connection tool corresponding portion 102*c* is interposed between the large one end part corresponding portion 102*a* and the inner end of the melted material inflow passage (runner channel) 104 in the casting cavity 102 of the main mold 100, but it is possible to remove the connection tool corresponding portion 102*c* and to connect the inner end of the melted material inflow passage (runner channel) 104 directly to the end of the large one end part corresponding portion 102*a* opposite to the small other end part corresponding portion 102*b*, like the casting cavity 12 of the main mold 10 of the first embodiment described with reference to FIGS. 1A to 1C.

In this case, after the ultrasonic transmission member 106 is taken out from the casting cavity 102 of the main mold 100, it is necessary to form the connection tool 106*c* by machining the melted material inflow passage corresponding portion (not shown), like the case in which the ultrasonic transmission member 16 is formed from the casting cavity 12 of the main mold 10 according to the first embodiment described with reference to FIGS. 1A to 1C. During this machining work, various known cooling actions, such as application of a cooling medium including a cooling liquid, must be applied not to reach a temperature of the metallic glass of the melted material inflow passage corresponding portion not shown to the crystallization temperature thereof or higher (that is, the metallic glass keeps amorphous and is not crystallized).

The outer dimensions of the ultrasonic horn used for welding and utilizing ultrasonic wave, which is configured as one example of the ultrasonic transmission member 106 finally formed by the method for forming an ultrasonic transmission member according to this embodiment, are considerably larger than the outer dimensions of the ultrasonic probe for an endoscope, which is configured by the ultrasonic transmission member finally formed by each of the various methods for forming ultrasonic transmission members according to the various embodiments of the present invention or by each of the various modifications of these methods, shown in FIGS. 1A to 9E.

Accordingly, when the whole of the ultrasonic transmission member 106 is formed with the metallic glass, like the method for forming an ultrasonic transmission member according to this embodiment, even if various heat radiation and/or cooling structures (not shown) are applied to the main mold 100, such a possibility occurs that the melted alloy 18, which is the material of the metallic glass and which is poured into the casting cavity 102, cannot be solidified in a liquid phase state in the vicinity of the center of the casting cavity 102 of the main mold 100 (for example, it can not be cooled at a cooling rate of 10 K/sec or more).

A method for forming an ultrasonic transmission member which can eliminate such a possibility as described above is a seventh embodiment described below.

Seventh Embodiment

Next, a method for forming an ultrasonic transmission member according to a seventh embodiment of the present invention will be explained with reference to FIGS. 11A to 11C.

Figure 11A:
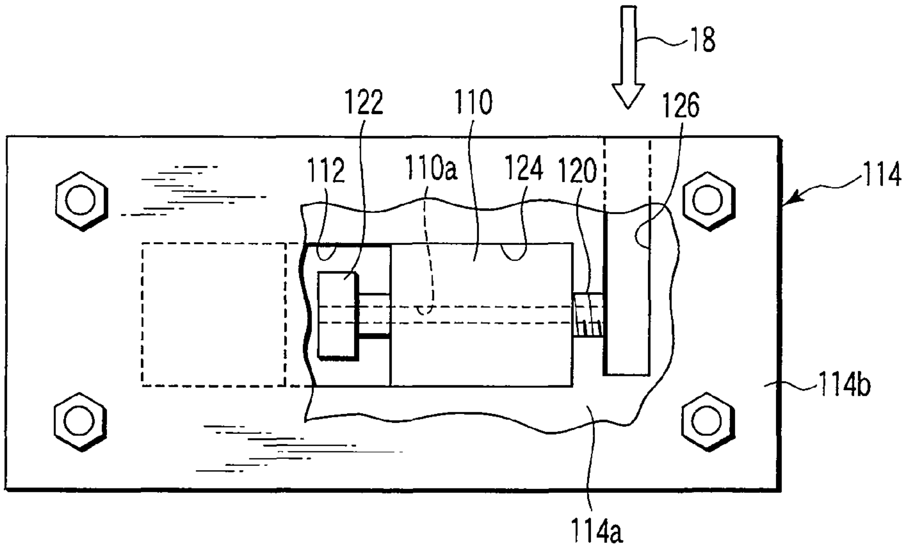
FIG. 11A is a schematic side view of a predetermined area formation mold used for a method for forming an ultrasonic transmission member according to a seventh embodiment of the present invention, where a part of the predetermined area formation mold is cut to show an ultrasonic transmission member main body disposed adjacent to a predetermined area formation casting cavity for forming a predetermined area in the predetermined area forming mold.
Figure 11B:
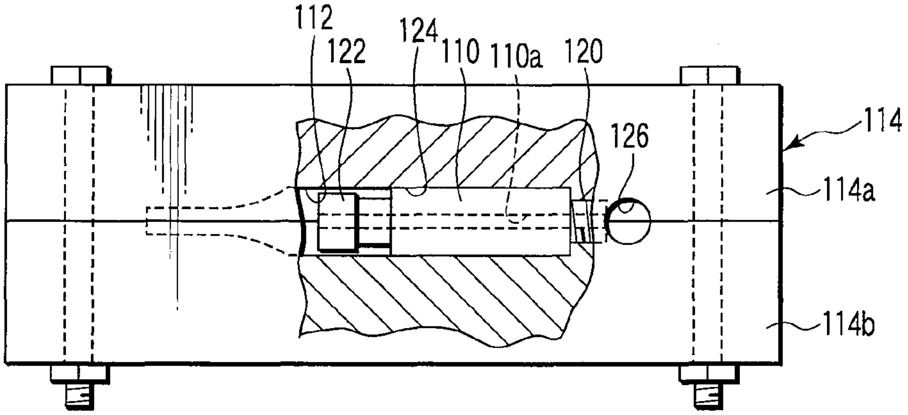
FIG. 11B is a schematic top view showing the predetermined area formation mold shown in FIG. 11A with a part of which is cut.

At first in this method, as shown in FIG. 11A, an ultrasonic transmission member main body 110 having a whole shape of desired dimensions for ultrasonic transmission except for a predetermined area is prepared and also a predetermined area formation mold 114 having a casting cavity 112 corresponding to an outer shape of the predetermined area is prepared.

The predetermined area formation mold 114 is a laterally-divided type having divided surfaces spreading in a vertical direction, and is formed with a metal having a high thermal conductivity, such as copper. The two half lateral pieces 114*a*, 114*b* of the predetermined area formation mold 114 are symmetrical to each other and are fixed to each other in a separable manner by a known separable fixing structure, for example, a combination of bolts and nuts. The casting cavity 112 is formed in the divided surfaces of the two half lateral pieces 114*a*, 114*b* of the predetermined area formation mold 114 in a vertically partitioned manner.

Figure 11C:
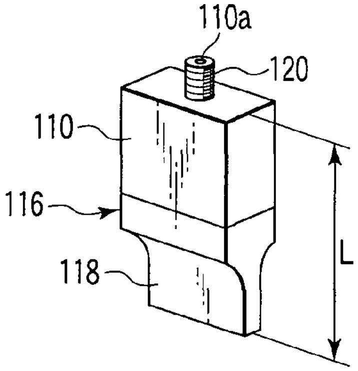
FIG. 11C is a schematic side view of a whole ultrasonic transmission member configured by joining a predetermined area, which is formed with metallic glass by using the predetermined area mold schematically shown in FIGS. 11A and 11B, to the ultrasonic transmission member main body disposed in the predetermined area mold.

A whole outer shape of an ultrasonic transmission member 116 finally formed by the method for forming an ultrasonic transmission member according to this embodiment is shown in FIG. 11C. The ultrasonic transmission member 116 has an ultrasonic transmission member main body 110 configuring a major portion of one end part of a large rectangular shape and a predetermined area 118 configuring the remaining portion of the one end part of the large rectangular shape and an other end part of a small rectangular shape. In the predetermined area 118, an area of the other end part positioned adjacent to the remaining portion of the one end part is gradually thickened and connects to the remaining portion of the one end part. That is, the predetermined area 118 of the ultrasonic transmission member 116 has substantially a wedge shape as a whole. Such an ultrasonic transmission member 116 configures an ultrasonic horn transmitting an ultrasonic wave input into the ultrasonic transmission member main body 110 configuring the major portion of the one end part to the predetermined area 118 configuring the other end part of the ultrasonic transmission member 116. Such an ultrasonic horn is used for welding utilizing an ultrasonic wave, for example.

A connection tool 120 for connecting the ultrasonic transmission member 116 to an ultrasonic generator (not shown) is formed on a side of the ultrasonic transmission member main body 110 opposite to the predetermined area 118. In this embodiment, the connection tool 120 is a male screw.

An ultrasonic wave with a predetermined frequency is input into the ultrasonic transmission member main body 110 of the ultrasonic transmission member 116 from the ultrasonic generator (not shown) connected to the connection tool 120, and it is preferable that a length L from an end surface of the ultrasonic transmission member main body 110 positioned on a side thereof opposite to the predetermined area 118 to a terminal end of the predetermined area 118 is integer times of a half ($\lambda/2$) of one wavelength $\lambda$ of the ultrasonic wave. Such an ultrasonic transmission member 116 is used in an ultrasonic (high frequency) welding machine.

Further, it is preferable that an end of the remaining portion of the one end part of the large rectangular shape of the predetermined area 118 of the ultrasonic transmission member 116 on the side of the small other end part (that is, a starting position of transition from the large one end part to the small other end part on an outer peripheral surface of the ultrasonic transmission member 116) substantially coincides with a node of an ultrasonic wave input into the one end part of the ultrasonic transmission member 116 from the ultrasonic generator (not shown) connected to the connection tool 120.

An anchor structure 122 for fixing with the predetermined area 118 formed by the casting cavity 112 of the predetermined area formation mold 114 is further provided on a side of the ultrasonic transmission member main body 110 opposite to the connection tool 120. In this embodiment, the anchor structure 122 have a strut with a small diameter and projecting from the abovementioned opposite side of the ultrasonic transmission member main body 110 and a disk with an increased diameter at a distal end of the strut. However, the anchor structure 122 can be any of various known shapes as long as it can fix the predetermined area 118 formed by the casting cavity 112 of the predetermined area formation mold 114 to the abovementioned opposite side of the ultrasonic transmission member main body 110.

A through-hole 110*a* is formed in the ultrasonic transmission member main body 110 so that it extends from a terminal end of the connection tool 120 to a terminal end of the anchor structure 122 (that is, a top of an umbrella).

The ultrasonic transmission member main body 110 is formed by machining a metal material such as titanium, titanium alloy, aluminum alloy, or nickel-aluminum ally, as an ultrasonic horn conventionally used.

The predetermined area formation mold 114 also has an ultrasonic transmission member main body accommodating space 124 having the same outer shape as that of the ultrasonic transmission member main body 110 to accommodate the ultrasonic transmission member main body 110. The ultrasonic transmission member main body accommodating space 124 is formed in the divided surfaces of the two half lateral pieces 114*a* and 114*b* of the predetermined area formation mold 114 in a vertically partitioned manner. The ultrasonic transmission member main body accommodating space 124 is disposed adjacent to a terminal end of the area of the casting cavity 112, the area corresponding to the remaining portion of the one end part of the large rectangular shape in the casting cavity 112.

The connection tool 120 of the ultrasonic transmission member main body 110 is disposed in a side of the ultrasonic transmission member main body accommodating space 124 opposite to the casting cavity 112. An inner end of a melted material inflow passage (runner channel) 126 formed in the predetermined area formation mold 114 communicates with the ultrasonic transmission member main body accommodating space 124 at a position corresponding to a terminal end of the connection tool 120 of the ultrasonic transmission member main body 110. The melted material inflow passage (runner channel) 126 is also formed in the divided surfaces of the two half lateral pieces 114*a* and 114*b* of the predetermined area formation mold 114 in the vertically partitioned manner.

The melted alloy 18 which is the material of the metallic glass is poured into an outer end (pouring gate) of the melted material inflow passage (runner channel) 126. The melted alloy 18 can be poured into the outer end (pouring gate) of the melted material inflow passage (runner channel) 126 by the gravity or by utilizing the melted metal pressurizing-injecting mechanism 24 used in the second modification of the method for forming an ultrasonic transmission member according to the first embodiment of the present invention described with reference to FIGS. 3A and 3B.

The melted alloy 18 poured into the melted material inflow passage (runner channel) 126 reaches the casting cavity 112 through the through-hole 110*a* of the ultrasonic transmission member main body 110 accommodated in the ultrasonic transmission member main body accommodating space 124 of the predetermined area formation mold 114, and is charged in the casting cavity 112.

Various known heat-radiating and/or cooling structures (not shown) are applied to the predetermined area formation mold 114 such that the melted alloy 18, which is the material of the metallic glass and which has been filled in the casting cavity 112 and the through-hole 110*a*, and further, preferably, into the melted material inflow passage (runner channel) 126, is solidified in a liquid phase state. As a result, the melted alloy 18, which has been filled in the casting cavity 112 and the through-hole 110*a*, and further, preferably, in the melted material inflow passage (runner channel) 126, is cooled at a cooling rate of 10 K/sec or more. The melted alloy 18 which has been poured as described above is cooled in this manner to be changed into an amorphous alloy (so-called "metallic glass") where no crystalline grain boundary is present, so that shapes and dimensions of the casting cavity 112 and the through-hole 110*a*, and further, preferably, those of the melted material inflow passage (runner channel) 126 are transferred to the amorphous alloy (so-called "metallic glass") precisely.

The predetermined area 118 made with the metallic glass, which has been in a glass solidification range in the casting cavity 112 of the predetermined area formation mold 114 and which has been transferred with the shape of the casting cavity 112, surrounds the anchor structure 122 of the ultrasonic transmission member main body 110 accommodated in the ultrasonic transmission member main body accommodating space 124 adjacent to the casting cavity 112 in the predetermined area formation mold 114 and is fixed to the ultrasonic transmission member main body 110.

Thus, the predetermined area 118 fixed to the ultrasonic transmission member main body 110 by the anchor structure 122, together with the ultrasonic transmission member main body 110, is taken out from the predetermined area formation mold 114 after further heat radiation for a predetermined time period. At this time, a melted material inflow passage corresponding portion (not shown) having a shape corresponding to the melted material inflow passage (runner channel) 126 is adhered to the connection tool 120 of the ultrasonic transmission member main body 110, but the melted material inflow passage corresponding portion is cut off from the connection tool 120 by a known cutoff apparatus.

As a result, the ultrasonic transmission member 116 serving as an ultrasonic horn shown in FIG. 11C is completed.

Incidentally, in this embodiment, the inner end of the melted material inflow passage (runner channel) 126 in the predetermined area formation mold 114 communicates with the ultrasonic transmission member main body accommodating space 124 at the position corresponding to the terminal end of the connection tool 120 of the ultrasonic transmission member main body 110, and further communicates with the casting cavity 112 in the predetermined area formation mold 114 through the through-hole 110*a* of the ultrasonic transmission member main body 110 accommodated in the ultrasonic transmission member main body accommodating space 124. However, it is possible to connect the inner end of the melted material inflow passage (runner channel) 126 directly to the terminal end of the casting cavity 112 (that is, the end of the casting cavity 112 on the side opposite to the ultrasonic transmission member main body accommodating space 124) and to remove the through-hole 110*a* in the ultrasonic transmission member main body 110.

First to Fourth Modifications of Seventh Embodiment

Next, first to fourth modifications of the anchor structure 122 of the ultrasonic transmission member main body 110, which is used in the method for forming an ultrasonic transmission member according to the seventh embodiment of the present invention described with reference to FIGS. 11A to 11C will be explained with reference to FIGS. 12A to 12D.

Figure 12A:
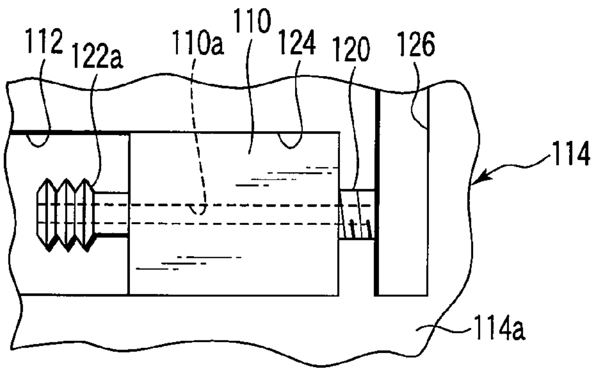
FIG. 12A is an enlarged schematic side view of a first modification of an anchor structure of an ultrasonic transmission member main body used in the method for forming an ultrasonic transmission member according to the seventh embodiment of the present invention, described above while referring to FIGS. 11A to 11C.

An anchor structure 122*a* according to the first modification and shown in FIG. 12A has a strut with a small diameter projecting from the side of the ultrasonic transmission member main body 110 opposite to the connection tool 120, and a plurality of expanding members expanding diametrically at a plurality of positions (three positions in FIG. 12A) on a distal end portion of the strut arranged in a longitudinal direction of the strut. The cross section of each of the expanding members of the anchor structure 122*a* according to the first modification can take any shape as long as the predetermined area 118 (see FIG. 11C) formed by the casting cavity 112 of the predetermined area formation mold 114 can be fixed to the abovementioned opposite side of the ultrasonic transmission member main body 110.

Figure 12B:
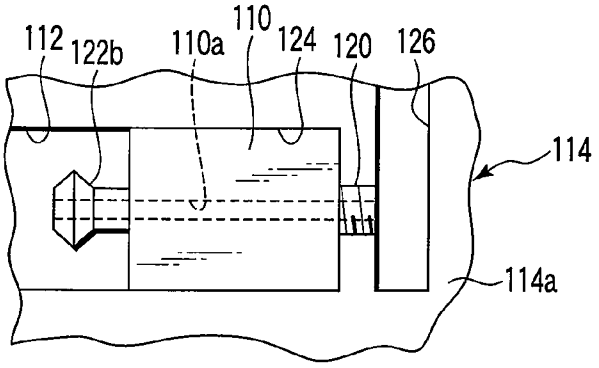
FIG. 12B is an enlarged schematic side view of a second modification of the anchor structure of the ultrasonic transmission member main body used in the method for forming an ultrasonic transmission member according to the seventh embodiment of the present invention, described above while referring to FIGS. 11A to 11C.

An anchor structure 122*b* according to the second modification and shown in FIG. 12B has a strut with a small diameter projecting from the side of the ultrasonic transmission member main body 110 opposite to the connection tool 120, and an expanding member expanding diametrically at a distal end of the strut. A cross section of the expanding member of the anchor structure 122*b* according to the second modification has a shape different from a cross section of the disk, which is one kind of the expanding member at the distal end of the strut of the anchor structure 122 of the ultrasonic transmission member main body 110 according to the seventh embodiment described with reference to FIGS. 11A and 11B, and the anchor structure 122*b* can take any shape as long as the predetermined area 118 (see FIG. 11C) formed by the casting cavity 112 of the predetermined area formation mold 114 can be fixed to the abovementioned opposite side of the ultrasonic transmission member main body 110.

Figure 12C:
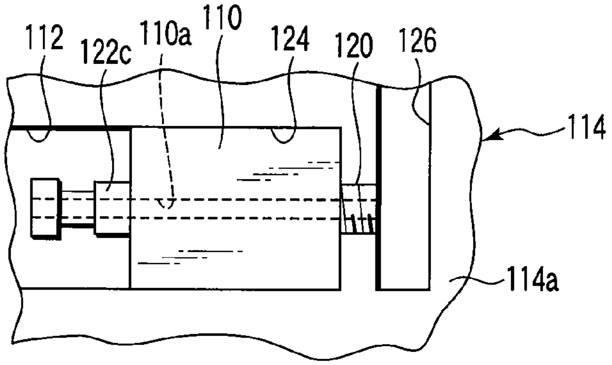
FIG. 12C is an enlarged schematic side view of a third modification of the anchor structure of the ultrasonic transmission member main body used in the method for forming an ultrasonic transmission member according to the seventh embodiment of the present invention, described above while referring to FIGS. 11A to 11C.

An anchor structure 122*c* according to the third modification and shown in FIG. 12C has a strut base with a large diameter projecting from the side of the ultrasonic transmission member main body 110 opposite to the connection tool 120, a strut with a small diameter projecting from a projecting end of the strut base, and an expanding member diametrically expanding at a distal end of the strut. The expanding member of the anchor structure 122*c* according to the third modification has a disk shape, but it may take any shape as long as the predetermined area 118 (see FIG. 11C) formed by the casting cavity 112 of the predetermined area formation mold 114 can be fixed to the abovementioned opposite side of the ultrasonic transmission member main body 110.

Figure 12D:
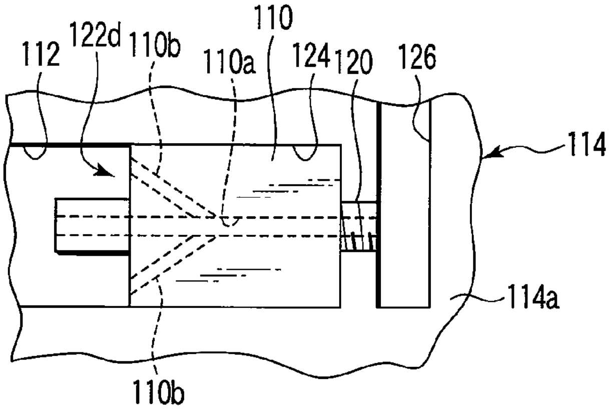
FIG. 12D is an enlarged schematic side view of a fourth modification of the anchor structure of the ultrasonic transmission member main body used in the method for forming an ultrasonic transmission member according to the seventh embodiment of the present invention, described above while referring to FIGS. 11A to 11C.

An anchor structure 122*d* according to the fourth modification shown in FIG. 12D is provided with a strut projecting from the side of the ultrasonic transmission member main body 110 opposite to the connection tool 120 and a plurality of branching holes 110*b* extending from the surrounding of the through-hole 110*a* on the abovementioned opposite side of the ultrasonic transmission member main body 110 toward the inside of the through hole 110*a*, and inner ends of the plurality of branching holes 110*b* communicate with the inside of the through-hole 110.

In this anchor structure 122*d*, while the melted metal alloy 18 (see FIG. 11A) which is the material of the metallic glass and which has been poured into the melted material inflow passage (runner channel) 126 is filled into the casting cavity 112 through the through-hole 110*a* of the ultrasonic transmission member main body 110 accommodated in the ultrasonic transmission member main body accommodating space 124 of the predetermined area formation mold 114, the abovementioned melted alloy 118 (see FIG. 11A) is further filled into the plurality of branching holes 110*b* through the through-hole 110*a*. The melted alloy 18 in the plurality of branching holes 110*b*, together with the melted alloy 18 in the casting cavity 112 of the predetermined area formation mold 114 and that in the through-hole 110*a* of the ultrasonic transmission member main body 110*a* and that in the melted material inflow passage (runner channel) 126, is in a glass solidification range, so that it fix the ultrasonic transmission member main body 110 to the predetermined area 118 (see FIG. 11C) formed in the casting cavity 112, like a root of a tree. Conversely, the predetermined area 118 (see FIG. 11C) formed in the casting cavity 112 is fixed to the ultrasonic transmission member main body 110 by the metallic glass, which has been changed from the melted alloy 18 in the glass solidification range, in the plurality of branched holes 110*b*.

Each of the plurality of branching holes 110*b* of the anchor structure 122*d* according to the fourth modification takes any of various shapes, as long as it satisfies the following condition. The condition is that, while the melted alloy 18 (see FIG. 11A), which is the material of the metallic glass and which has been poured into the melted material inflow passage (runner channel) 126, is filled into the casting cavity 112 through the through-hole 110*a* of the ultrasonic transmission member main body 110 accommodated in the ultrasonic transmission member main body accommodating space 124 of the predetermined area formation mold 114, the abovementioned melted alloy 18 (see FIG. 11A) can be filled into each of the plurality of branching holes 110*b* through the through-hole 110*a*, and further, after the abovementioned melted alloy 18 in each of the plurality of branching holes 110*b* changes to metallic glass in the glass solidification range, it can sufficiently fix the predetermined area 118 (see FIG. 11C), formed with the metallic glass which has been changed from the abovementioned melted alloy 18 in the glass solidification range in the casting cavity 112 of the predetermined area formation mold 114, to the abovementioned opposite side of the ultrasonic transmission member main body 110.

Eighth Embodiment

Next, a method for forming an ultrasonic transmission member according to an eighth embodiment of the present invention will be explained with reference to FIGS. 13A to 13D.

Figure 13A:
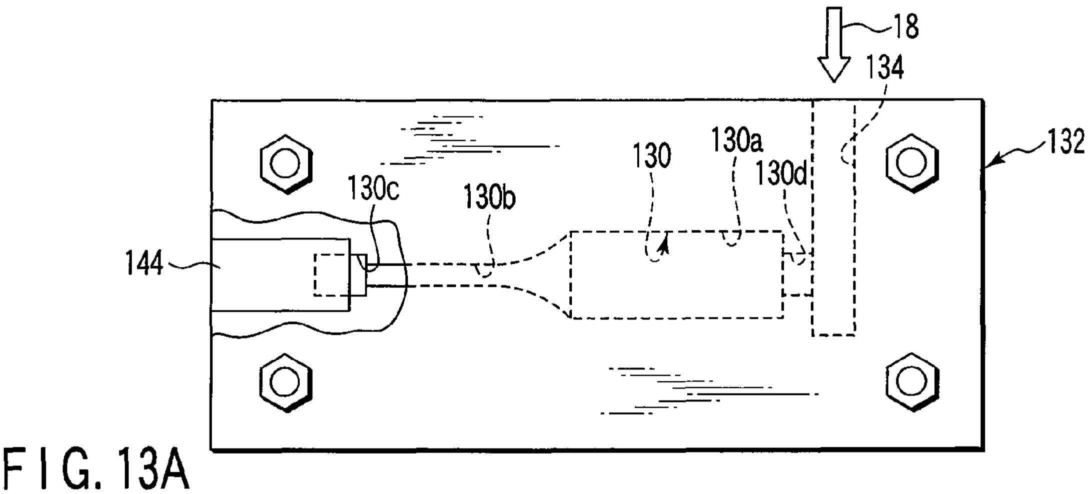
FIG. 13A is a schematic side view showing a mold used in a method for forming an ultrasonic transmission member according to an eighth embodiment of the present invention, a part of the mold being cut.
Figure 13B:
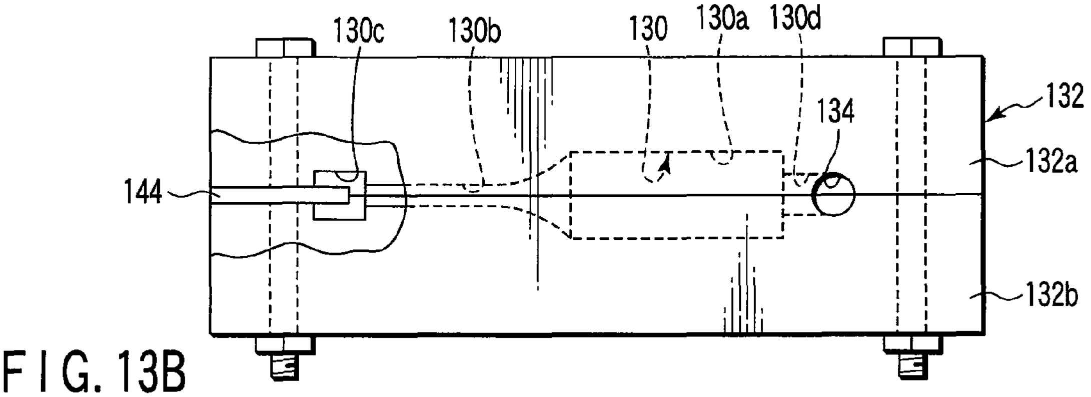
FIG. 13B is a schematic top view of the main mold shown in FIG. 13A.
Figure 13C:
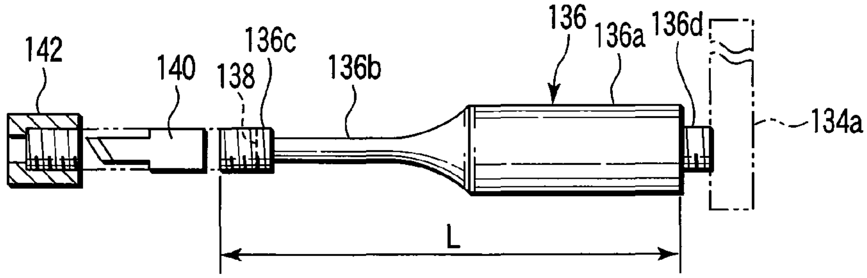
FIG. 13C is a schematic side view showing an ultrasonic transmission member formed with metallic glass by using the main mold schematically shown in FIGS. 13A and 13B, together with a tool to be fixed to the ultrasonic transmission member for use and a tool fixing element used for the fixation, in a state that they are separated from one another.
Figure 13D:
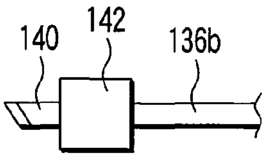
FIG. 13D is a schematic partial side view showing a state that the tool is fixed to the ultrasonic transmission member illustrated In FIG. 13C by the tool fixing element.

As shown in FIG. 13A, a main mold 132 having a casting cavity 130 is prepared. The main mold 132 further has a melted material inflow passage (runner channel) 134 for communicating the casting cavity 130 with the outer space. The casting cavity 130 has a shape corresponding to a whole outer shape and outer dimensions of a desired ultrasonic transmission member 136 whose side face is shown in FIG. 13C.

In this embodiment, the desired ultrasonic transmission member 136 has one end part 136*a* with a large diameter, the other end part 136*b* with a small diameter, and a tool fixing part 136*c* formed on a side of the other end part 136*b* with a small diameter opposite to the one end part 136*a* with a large diameter, and transmits ultrasonic wave input into the one end part 136*a* up to the other end part 136*b*. Such an ultrasonic transmission member 136 configures an ultrasonic horn. The tool fixing part 136*c* is formed on the side of the other end part 136*b* with a small diameter opposite to the one end part 136*a* with a large diameter. Such an ultrasonic horn is used as a tool-ultrasonic driving apparatus for activating a tool fixed to the tool fixing part 136*c* by utilizing ultrasonic wave.

In this embodiment, the tool fixing part 136*c* includes a tool holding slit 138 extending from a terminal end of the tool fixing part 136 in a longitudinal direction of the other end part 136*b* and crossing the tool fixing part 136*c* in its diametrical direction. A base portion of a tool 140, such as a knife, is held in the tool holding slit 138. The base portion of the tool 140 held in the tool holding slit 138 is fixed to the tool fixing part 136*c* by a tool fixing element 142 being capped on an outer peripheral surface of the tool fixing part 136*c* and being fixed thereto. The tool fixing element 142 has an opening for exposing a tip end portion of the tool 140 held in the tool holding slit 138. It is preferable that the tool fixing element 142 is detachably capped on and fixed to the outer peripheral surface of the tool to fixing part 136*c* by a known fixing structure. Therefore, in this embodiment, a male screw is formed on the outer peripheral surface of the tool fixing part 136*c*, and a female screw to be screwed on the male screw on the outer peripheral surface of the tool fixing part 136*c* is formed on an inner peripheral surface of the tool fixing element 142. However, the abovementioned fixing can be performed with frictional engagement or an adhesive.

A connection tool 136*d* for connecting the ultrasonic transmission member 136 to an ultrasonic generator (not shown) is formed on a side of the large one end part 136*a* opposite to the small other end part 136*b*. In this embodiment, the connection tool 136*d* is a male screw.

An ultrasonic wave of a predetermined frequency is input into the one end part 136*a* of the ultrasonic transmission member 136 from the ultrasonic generator (not shown) connected to the connection tool 136*d*, and it is preferable that a length L from an end surface of the large one end part 136*a* on the side opposite to the small other end part 136*b* to an end surface of the tool supporting part 136*c* at a terminal end of the other end part 136*b* is integer times of a half (λ/2) of one wavelength λ of the ultrasonic wave.

Further, it is preferable that an end of the large one end part 136*a* of the ultrasonic transmission member 136 on the side of the small other end part 136*b* (that is, a starting position of transition from the large one end part 136*a* to the small other end part 136*b* on an outer peripheral surface of the ultrasonic transmission member 136) substantially coincides with a node of the ultrasonic wave input into the one end part 136*a* of the ultrasonic transmission member 136 from the ultrasonic generator (not shown) connected to the connection tool 136*d*.

The casting cavity 130 in this embodiment includes a one end part corresponding portion 130*a* corresponding to the large one end part 136*a* of the ultrasonic transmission member 136, an other end part corresponding portion 130*b* corresponding to the small other end part 136*b* of the ultrasonic transmission member 136, a tool fixing part corresponding portion 130*c* corresponding to the tool fixing part 136*c* of the ultrasonic transmission member 136, and a connection tool corresponding portion 130*d* corresponding to the connection tool 136*d* of the ultrasonic transmission member 136.

The main mold 132 is a laterally-divided type having divided surfaces spreading in a vertical direction, and is formed with a metal having a high thermal conductivity, such as copper. Two half lateral pieces 132*a* and 132*b* of the main mold 132 are symmetrical to each other, and are fixed to each other in a separable manner by a known separable fixing structure, for example, a combination of bolts and nuts. The casting cavity 130 and the melted material inflow passage (runner channel) 134 are formed in the divided surfaces of the two half lateral pieces 132*a* and 132*b* of the main mold 132 in a vertically partitioned manner.

The melted material inflow passage (runner channel) 134 has an outer end (pouring gate) opened in an upper surface of the main mold 132, and an inner end connected to a predetermined area of the casting cavity 130, namely, to a side of the connection tool corresponding portion 130*d* opposite to the one end part corresponding portion 130*a* in this embodiment.

A flat plate-like core member 144 is disposed in the casting cavity 130 of the main mold 132 so as to cross the tool fixing part corresponding portion 130*c* in its diametric direction. In this embodiment, the core member 144 is supported by the divided surfaces of the two half lateral pieces 132*a* and 132*b* of the main mold 132.

The melted alloy 18 which is the material of the metallic glass is poured into the outer end (pouring gate) of the melted material inflow passage (runner channel) 134. The melted alloy 18 can be poured into the outer end (pouring gate) of the melted material inflow passage (runner channel) 134 by the gravity or by utilizing the melted metal pressurizing-injecting mechanism 24 used in the second modification of the method for forming an ultrasonic transmission member according to the first embodiment of the present invention described with reference to FIGS. 3A and 3B.

Various known heat-radiating and/or cooling structures (not shown) are applied to the main mold 132 to solidify the melted alloy 18, which is the material of the metallic glass and which has been poured into the casting cavity 130 through the melted material inflow passage (runner channel) 134, in a liquid phase state. As a result, the melted alloy 18 which has been poured into the casting cavity 130 is cooled at a cooling rate of 10 K/sec or more. The melted alloy 18 which has been poured into the casting cavity 130 is cooled in this manner to be changed to an amorphous alloy (so-called "metallic glass") where no crystalline grain boundary is present, so that the shape and dimensions of the casting cavity 130 are transferred to the abovementioned amorphous alloy (so-called "metallic glass") precisely.

The ultrasonic transmission member 136 made with the metallic glass in the casting cavity 130, which has been in the glass solidification range and which has been transferred with the shape of the casting cavity 130, together with the core member 144, is taken out from the main mold 132 after further heat radiation for a predetermined time period. At this time, the ultrasonic transmission member 136 shown by a solid line in FIG. 13C accompanies the melted material inflow passage corresponding portion 134*a* having a shape corresponding to the melted material inflow passage (runner channel) 134 on the connection tool 136*d* as shown by a two-dots chain line in FIG. 13C.

Next, the core member 144 is withdrawn from the ultrasonic transmission member 136, and the melted material inflow passage corresponding portion 134*a* is removed from the connection tool 136*d* by machining. As a result, the ultrasonic transmission member 136 serving as an ultrasonic horn for a tool-ultrasonic driving apparatus shown in FIG. 13C is completed.

Incidentally, the connection tool corresponding portion 130*d* is interposed between the one end part corresponding portion 130*a* with a large diameter and the inner end of the melted material inflow passage (runner channel) 134 in the casting cavity 130 of the main mold 132, but it is possible to remove the connection tool corresponding portion 130*d* and to connect the inner end of the melted material inflow passage (runner channel) 134 directly with the end of the one end part corresponding portion 130*a* with a large diameter on the side opposite to the other end part corresponding portion 130*b* with a small diameter, like the casting cavity 12 of the main mold 10 of the first embodiment described with reference to FIGS. 1A to 1C.

In this case, after the ultrasonic transmission member block 136 is taken out from the casting cavity 130 of the mold 132 and the core member 144 is further withdrawn from the ultrasonic transmission member 136, it is necessary to form the connection tool 136*d* by machining the melted material inflow passage corresponding portion 134*a*, like the case in which the ultrasonic transmission member 16 is formed by the casting cavity 12 of the main mold 10 according to the first embodiment described with reference to FIGS. 1A to 1C. During this machining work, various known cooling actions, such as application of a cooling medium including a cooling liquid, must be applied not to reach a temperature of the metallic glass of the melted material inflow passage corresponding portion 134*a* to the crystallization temperature thereof or higher (that is, the metallic glass keeps amorphous and is not crystallized).

The tool holding slit 138 of the tool fixing part 136*c* of the ultrasonic transmission member 136 and the male screw on the outer peripheral surface of the tool fixing part 136*c* can be formed by machining after the ultrasonic transmission member 136 is taken out from the casting cavity 130 of the main mold 132, instead of the shape transfer performed by the core member 144 and by the tool fixing part corresponding portion 130*c* of the casting cavity 130 of the main mold 132. Also, during this machining work, various known cooling actions, such as application of a cooling medium including a cooling liquid, must be applied not to reach a temperature of the metallic glass of the tool fixing part corresponding portion 130*c* to crystallization temperature thereof or higher (that is, the metallic glass keeps amorphous and is not crystallized).

Modification of Eighth Embodiment

Figure 13E:
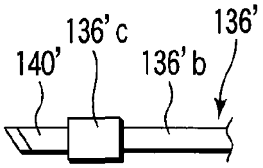
FIG. 13E is a schematic partial side view showing a state that a tool is integrally formed with an ultrasonic transmission member in a modification of the method for forming an ultrasonic transmission member according to the eighth embodiment of the present invention.

In FIG. 13E, a tool fixing part 136'*c* on the other end part 136'*b* with a small diameter of an ultrasonic transmission member 136' formed according to a modification of the method for forming an ultrasonic transmission member according to the eighth embodiment of the present invention described with reference to FIGS. 13A to 13D and a tool 140' fixed to the tool fixing part 136'*c* are schematically shown. Here, the tool 140' is integrally formed with the tool fixing part 136'*c* with the same material as that of the tool fixing part 136'*c*.

This modification is different from the eighth embodiment in that the casting cavity 130 of the main mold 132 has a tool corresponding portion on a side of the tool fixing part corresponding portion 130*c* opposite to the other end part corresponding portion 130*b*, and the core member 144 is not required.

Ninth Embodiment

Next, a method for forming an ultrasonic transmission member according to a ninth embodiment of the present invention will be explained with reference to FIGS. 14A and 14B.

Figure 14A:
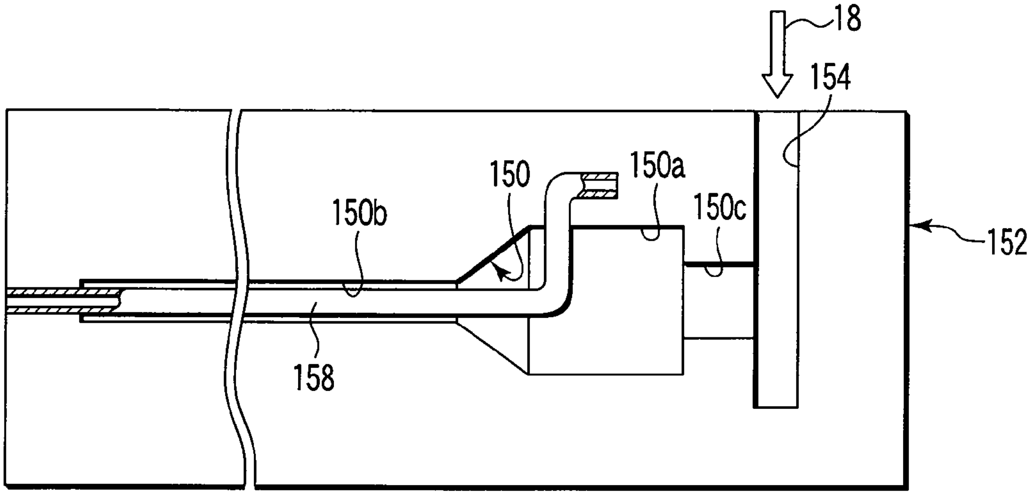
FIG. 14A is a side view schematically showing a half lateral piece of a main mold used in a method for forming an ultrasonic transmission member according to a ninth embodiment of the present invention, and an elongated hollow member disposed in a half casting cavity formed in the half lateral piece.

As shown in FIG. 14A, a main mold 152 having a casting cavity 150 is prepared. The main mold 152 also includes a melted material inflow passage (runner channel) 154 for communicating the casting cavity 150 with the outer space. The casting cavity 150 has a shape corresponding to a whole outer shape and outer dimensions of a desired ultrasonic transmission member 156 shown in FIG. 14B.

In this embodiment, the abovementioned desired ultrasonic transmission member 156 includes one end part 156*a* with a large diameter and the other end part 156*b* with a small diameter, and transmits an ultrasonic wave input into the one end part 156*a* up to the other end part 156*b*. Such an ultrasonic transmission member 156 configures an ultrasonic horn, and is used in a spray device in this embodiment.

A connection tool 156*c* for connecting the ultrasonic transmission member 156 with a known ultrasonic generator USG is formed on a side of the one end part 156*a* with a large diameter opposite to the other end part 156*b*. In this embodiment, the connection tool 156*c* is a male screw.

An ultrasonic wave with a predetermined frequency is input into the one end part 156*a* with a large diameter of the ultrasonic transmission member 156 configuring the abovementioned ultrasonic horn, from the ultrasonic generator USG connected to the connection tool 156*c*, and it is preferable that a length L from an end surface of the one end part 156*a* with a large diameter positioned on a side opposite to the other end part 156*b* to a terminal end of the other end part 156*b* with a small diameter is integer times of a half (λ/2) of one wavelength λ of the abovementioned ultrasonic wave.

Further, it is preferable that an end of the one end part 156*a* with a large diameter of the ultrasonic transmission member 156 positioned on the side of the other end part 156*b* with a small diameter (that is, a starting position of transition from the one end part 156*a* with a large diameter to the other end part 156*b* with a small diameter on an outer peripheral surface of the ultrasonic transmission member 156) substantially coincides with a node of the ultrasonic wave input into the one end part 156*a* of the ultrasonic transmission member 156 from the ultrasonic generator USG connected to the connection tool 156*c*.

The casting cavity 150 in this embodiment includes a one end part corresponding portion 150*a* corresponding to the one end part 156*a* with a large diameter of the ultrasonic transmission member 156, an other end part corresponding portion 150*b* corresponding to the other end part 156*b* with a small diameter of the ultrasonic transmission member 156, and a connection tool corresponding portion 150*c* corresponding to an outer shape of the connection tool 156*c* of the ultrasonic transmission member 156, and an inner end of the melted material inflow passage (runner channel) 154 is connected to a side of the connection tool corresponding portion 150*c* opposite to the one end part corresponding portion 150*a*.

The main mold 152 is a laterally-divided type having divided surfaces spreading in a vertical direction, and is formed with a metal having a high thermal conductivity, such as copper. Two half lateral pieces 152*a* of the main mold 152 are fixed to each other in a separable manner by a known separable fixing structure, for example, a combination of bolts and nuts. The two half lateral pieces 152*a* are symmetrical to each other, and only one of the two half lateral pieces 152*a* is shown in FIG. 14A. The casting cavity 150 and the melted material inflow passage (runner channel) 154 are formed in the divided surfaces of the two half lateral pieces 152*a* of the main mold1 152 in a vertically partitioned manner.

A pipe 158 extending from one end part of the casting cavity 150 to the other end part thereof (in this embodiment, from an inner peripheral surface of the one end part corresponding portion 150*a* to an outer end of a side of the other end part corresponding portion 150*b* opposite to the one end part corresponding portion 150*a*) is disposed in the casting cavity 150 of the main mold 152.

Specifically, the pipe 158 is prepared independently from the main mold 152. An end (a proximal end) of the pipe 158 positioned on the side of the one end part corresponding portion 150*a* projects from the inner peripheral surface of the one end part corresponding portion 150*a* in a radially outward direction of the one end part corresponding portion 150*a* in the casting cavity 150 of the main mold 154, while an end (an extended end) of the pipe 158 positioned on the side of the other end part corresponding portion 150*b* projects from an outer end of the other end part corresponding portion 150*b* outwardly in the longitudinal direction of the other end part corresponding portion 150*b* in the casting cavity 150 of the main mold 152.

The melted alloy 18 which is the material of the metallic glass is poured into the outer end (pouring gate) of the melted material inflow passage (runner channel) 154. The melted alloy 18 can be poured into the outer end (pouring gate) of the melted material inflow passage (runner channel) 154 by the gravity or by utilizing the melted metal pressurizing-injecting mechanism 24 used in the second modification of the method for forming an ultrasonic transmission member according to the first embodiment of the present invention described with reference to FIGS. 3A and 3B.

Various known heat-radiating and/or cooling structures (not shown) are applied to the main mold 152 to solidify the melted alloy 18, which is the material of the metallic glass and which has been poured into the casting cavity 150 through the melted material inflow passage (runner channel) 154, in a liquid phase state. As a result, the melted alloy 18 which has been poured into the casting cavity 150 is cooled at a cooling rate of 10 K/sec or more. The melted alloy 18 which has been poured into the casting cavity 150 is rapidly cooled in this manner, so that a shape and dimensions of the casting cavity 150 are transferred to the amorphous alloy (so-called "metallic glass") precisely.

The ultrasonic transmission member 156 made with the metallic glass, which has been in a glass solidification range and which has been transferred with the shape of the casting cavity 150, together with the pipe 158, is taken out from the main mold 152 after further heat radiation for a predetermined time period. At this time, the ultrasonic transmission member 156 shown by a solid line in FIG. 14B accompanies a melted material inflow passage corresponding portion with a shape corresponding to the melted material inflow passage (runner channel) 154 on the connection tool 156*c*.

Next, the melted material inflow passage corresponding portion is removed from the connection tool 156*c* by machining, and further a portion of the pipe 158 projecting from the outer end of the other end part 156*b* with a small diameter is removed by machining.

As a result, the ultrasonic transmission member 156 having a pipe 158 extending from the outer peripheral surface of the one end part 156*a* to the outer end of the other end part 156*b* with a small diameter and configuring the ultrasonic horn can be obtained.

Incidentally, the connection tool corresponding portion 150*c* is interposed between the one end part corresponding portion 150*a* with a large diameter and the inner end of the melted material inflow passage (runner channel) 154 in the casting cavity 150 of the main mold 152, and it is possible to remove the connection tool corresponding portion 150*c* and to connect the inner end of the melted material inflow passage (runner channel) 154 directly to the end of the one end part corresponding portion 150*a* with a large diameter positioned on the side opposite to the other end part corresponding portion 150*b* with a small diameter, like the casting cavity 12 of the main mold 10 of the first embodiment described with reference to FIGS. 1A to 1C.

In this case, after the ultrasonic transmission member 156 is taken out from the casting cavity 150 of the main mold 152, it is necessary to form the connection tool 156*c* by machining the melted material inflow passage corresponding portion, like the case in which the ultrasonic transmission member 16 is formed from the casting cavity 12 of the main mold 10 according to the first embodiment described with reference to FIGS. 1A to 1C. During this machining work, various known cooling actions, such as application of a cooling medium including a cooling liquid, must be applied not to reach a temperature of the metallic glass of the melted material inflow passage corresponding portion to the crystallization temperature thereof or higher (that is, the metallic glass keeps amorphous and is not crystallized).

Further, it is preferable that the proximal end portion of the pipe 158 projecting from the outer peripheral surface of the one end part 156*a* with a large diameter of the ultrasonic transmission member 156 is positioned at a node of the ultrasonic wave input from the ultrasonic generator USG into the one end part 156*a* of the ultrasonic transmission member 156.

Thereby, such a possibility can be remarkably reduced that the proximal end portion of the pipe 158 is damaged by vibrations of the ultrasonic wave input from the ultrasonic generator USG into the one end part 156*a* of the ultrasonic transmission member 156.

Figure 14B:
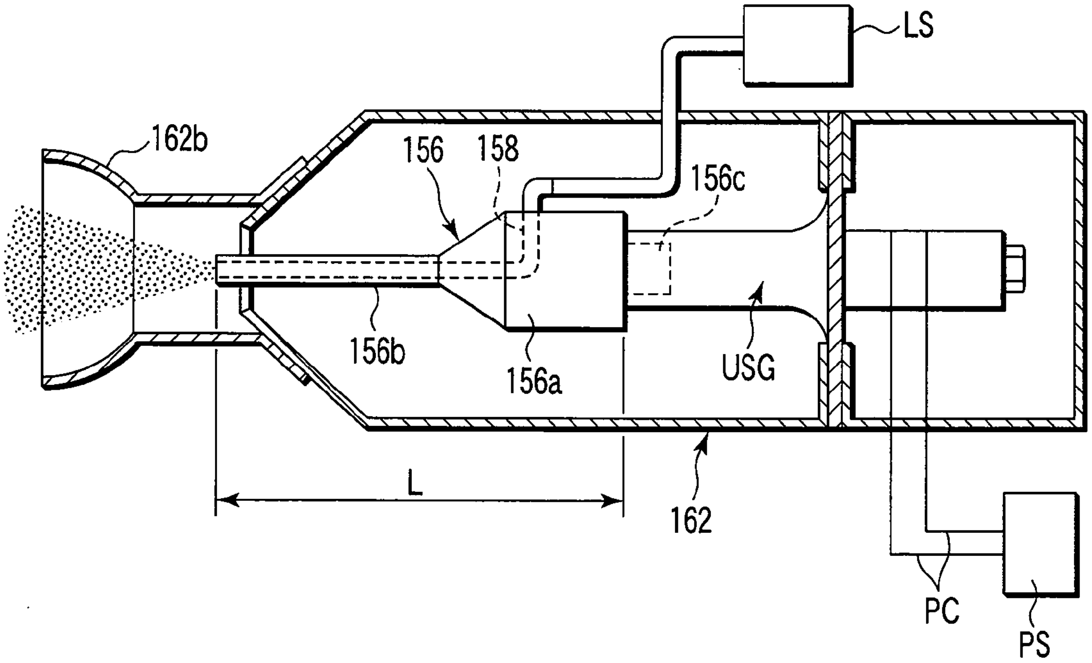
FIG. 14B is a schematic vertical sectional view of a spray device using an ultrasonic transmission member formed with metallic glass by the casting cavity of the main mold with the elongated hollow member shown in FIG. 14A.

As shown in FIG. 14B, the ultrasonic generator USG accompanying the ultrasonic transmission member 156 is disposed at a predetermined position in a housing 162 for the spray device 160. A power cable PC extends from the ultrasonic generator USG in the housing 162 to an outer power source for the ultrasonic generator (for example, an electric power source) PS, and a liquid supplying pipe LP extends from the proximal end of the pipe 158 of the ultrasonic transmission member 156 in the housing 162 to a liquid supplying source LS in an outside of the housing 162.

The pipe 158 of the ultrasonic transmission member 156 must be formed with a material which is not changed by a liquid supplied from the liquid supplying source LS through the liquid supplying pip LP, and the liquid can be any desired kind.

The housing 162 includes an opening 162*a* for exposing the outer end of the other end part 156*b* with a small diameter of the ultrasonic transmission member 156 to the outer space and is provided with a cover 162*b* surrounding the opening 162*a*.

When power is supplied from the power source for the ultrasonic generator (for example, the electric power source) PS to the ultrasonic generator USG through the power cable PC, an ultrasonic wave generated by the ultrasonic generator USG is input into the one end part 156*a* with a large diameter of the ultrasonic transmission member 156 and is further transmitted up to the outer end of the other end part 156*b* with a small diameter of the ultrasonic transmission member 156. At this time, when a liquid is supplied from the liquid supplying source LS to the pipe 158 of the ultrasonic transmission member 156 through the liquid supplying pipe LP, the liquid is atomized and discharged from the outer end of the pipe 158 at the outer end of the other end part 156*b* with a small diameter 156*b* of the ultrasonic transmission member 156 which is vibrated by the ultrasonic wave.

Tenth Embodiment

Next, a method for forming an ultrasonic transmission member according to a tenth embodiment of the present invention will be explained with reference to FIGS. 15A to 15C.

Figure 15A:
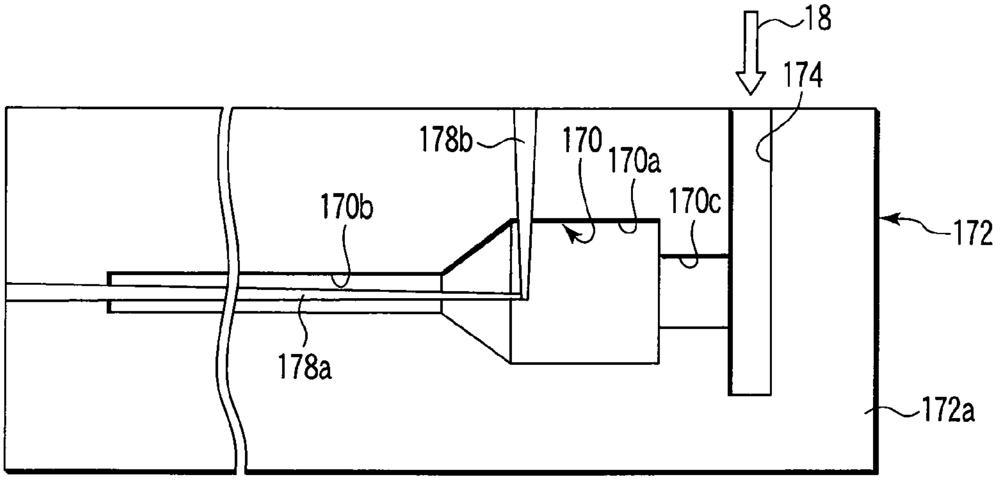
FIG. 15A is a side view schematically showing a half lateral piece of a main mold used in a method for forming an ultrasonic transmission member according to a tenth embodiment of the present invention, and elongated and tapered core members disposed in a half casting cavity formed in the half lateral piece.

As shown in FIG. 15A, a main mold 172 having a casting cavity 170 is prepared. The main mold 152 further has a melted material inflow passage (runner channel) 174 for communicating the casting cavity 170 with the outer space. The casting cavity 170 has a shape corresponding to a whole outer shape and outer dimensions of a desired ultrasonic transmission member 176 shown in FIG. 15B.

In this embodiment, the desired ultrasonic transmission member 176 has one end part 176*a* with a large diameter and the other end part 176*b* with a small diameter, and transmits an ultrasonic wave input into the one end part 176*a* up to the other end part 176*b*. Such an ultrasonic transmission member 176 configures an ultrasonic horn, and can be used instead of the ultrasonic transmission member 156 used in the spray device 160 shown in FIG. 14B, for example.

A connection tool 176*c* for connecting the ultrasonic transmission member 176 with the known ultrasonic generator USG shown in FIG. 14B is formed on a side of the one end part 176*a* with a large diameter opposite to the other end part 176*b*. In this embodiment, the connection tool 176*c* is a male screw.

The ultrasonic wave with the predetermined frequency is input into the one end part 176*a* with a large diameter of the ultrasonic transmission member 176 configuring the abovementioned ultrasonic horn from the ultrasonic generator USG connected to the connection tool 176*c*, and it is preferable that a length L from an end surface of the one end part 176*a* with a large diameter on the side opposite to the other end part 176*b* with a small diameter to a terminal end of the other end part 176*b* with a small diameter is integer times of a half (λ/2) of one wavelength λ of the abovementioned ultrasonic wave.

Further, it is preferable that an end of the one end part 176*a* with a large diameter of the ultrasonic transmission member 176 on the side of the other end part 176*b* with a small diameter (that is, a starting position of transition from the one end part 176*a* with a large diameter to the other end part 176*b* with a small diameter on an outer peripheral surface of the ultrasonic transmission member 176) substantially coincides with a node of the ultrasonic wave input into the one end part 176*a* of the ultrasonic transmission member 176 from the ultrasonic generator USG connected to the connection tool 176*c*.

The casting cavity 170 in this embodiment includes a one end part corresponding portion 170*a* corresponding to the one end part 176*a* with a large diameter of the ultrasonic transmission member 176, an other end part corresponding portion 170*b* corresponding to the other end part 176*b* with a small diameter of the ultrasonic transmission member 176, and a connection tool corresponding portion 170*c* corresponding to an outer shape of the connection tool 176*c* of the ultrasonic transmission member 176, and an inner end of the melted material inflow passage (runner channel) 174 is connected to a side of the connection tool corresponding portion 170*c* opposite to the one end part corresponding portion 170*a*.

The main mold 172 is a laterally-divided type having divided surfaces spreading in a vertical direction, and is formed with a metal having a high thermal conductivity, such as copper. Two half lateral pieces 172*a* of the main mold 172 are fixed to each other in a separable manner by a known separable fixing structure, for example, a combination of bolts and nuts. The two half lateral pieces 172*a* are symmetrical to each other, and only one of the two half lateral pieces 172*a* is shown in FIG. 15A. The casting cavity 170 and the melted material inflow passage (runner channel) 174 are formed in the divided surfaces of the two half lateral pieces 172*a* of the main mold 172 in a vertically partitioned manner.

In the casting cavity 170 of the main mold 172, an elongated first core configuring element 178*a* extending from an outer end of the other end part corresponding portion 170*b* of the casting cavity 170 on a side opposite to the one end part corresponding portion 170*a* into the one end part corresponding portion 170*b* of the casting cavity 170 and an elongated second core configuring element 178*b* extending from an inner peripheral surface of the one end part corresponding portion 170*a* in a radially inward direction of the one end part corresponding portion 170*a* are disposed. Respective outer end portions of the first core configuring element 178*a* and the second core configuring element 178*b* are supported by the main mold 172, and respective inner end portions of the first core configuring element 178*a* and the second core configuring element 178*b* abut on each other in the one end part corresponding portion 170*a*.

Respective peripheral surfaces of the first core configuring element 178*a* and the second core configuring element 178*b* are tapered such that they are gradually reduced in diameter from the abovementioned outer end portions toward the abovementioned inner end portions. The first core configuring element 178*a* and the second core configuring element 178*b* configure an elongated core member extending from the one end part corresponding portion 170*a* to the other end part corresponding portion 170*b* in the casting cavity 170 of the main mold 172.

The melted alloy 18 which is the material of the metallic glass is poured into an outer end (pouring gate) of the melted material inflow passage (runner channel) 174. The melted alloy 18 can be poured into the outer end (pouring gate) of the melted material inflow passage (runner channel) 174 by the gravity or by utilizing the melted metal pressurizing-injecting mechanism 24 used in the second modification of the method for forming an ultrasonic transmission member according to the first embodiment of the present invention described with reference to FIGS. 3A and 3B.

Various known heat-radiating and/or cooling structures (not shown) are applied to the main mold 172 to solidify the melted alloy 18, which is the material of the metallic glass and which has been poured into the casting cavity 170 through the melted material inflow passage (runner channel) 174, in a liquid phase state. As a result, the melted alloy 18 which has been poured into the casting cavity 170 is cooled at a cooling rate of 10 K/sec or more. The melted alloy 18 which has been poured into the casting cavity 170 is cooled in this manner, so that a shape and dimensions of the casting cavity 170 are transferred to the abovementioned amorphous alloy (so-called "metallic glass") precisely.

The ultrasonic transmission member 176 formed with the metallic glass, which has been in the glass solidification zone in the casting cavity 170 and which has been transferred with the shape of the casting cavity 170, together with the first and second core configuring elements 178*a* and 178*b*, is taken out from the main mold 172 after further heat radiation for a predetermined time period. At this time, the ultrasonic transmission member 176 shown by a solid line in FIG. 15B accompanies the melted material inflow passage corresponding portion 174*a* having a shape corresponding to the melted material inflow passage (runner channel) 174 on the connection tool 176*c*.

Next, the melted material inflow passage corresponding portion 174*a* is removed from the connection tool 176*c* by machining, and the first and second core configuring elements 178*a* and 178*b* are withdrawn from the ultrasonic transmission member 176.

As a result, after the first and second core configuring elements 178*a* and 178*b* are withdrawn from the ultrasonic transmission member 176, a through-hole 180 extending from the outer peripheral surface of the one end part 176*a* with a large diameter to the outer end of the other end part 176*b* with a small diameter is remained. That is, the ultrasonic transmission member 176 formed as described above and configuring the ultrasonic horn has the through-hole 180.

Incidentally, the connection tool corresponding portion 170*c* is interposed between the one end part corresponding portion 170*a* with a large diameter and the inner end of the melted material inflow passage (runner channel) 174 in the casting cavity 170 of the main mold 172, but it is possible to remove the connection tool corresponding portion 170*c* and to connect the inner end of the melted material inflow passage (runner channel) 174 directly to the end of the one end part corresponding portion 170*a* with a large diameter on the side opposite to the other end part corresponding portion 170*b* with a small diameter, like the casting cavity 12 of the main mold 10 of the first embodiment described with reference to FIGS. 1A to 1C.

In this case, after the ultrasonic transmission member 176 is taken out from the casting cavity 170 of the main mold 172 and the first and second core configuring elements 178_a_ and 178_b_ are withdrawn from the ultrasonic transmission member 176, it is necessary to form the connection tool 176_c_ by machining the melted material inflow passage corresponding portion 174_a_, like the case in which the ultrasonic transmission member 16 is formed by the casting cavity 12 of the main mold 10 according to the first member described with reference to FIGS. 1A to 1C. During this machining work, various known cooling actions, such as application of a cooling medium including a cooling liquid, must be applied not to reach a temperature of the metallic glass of the melted material inflow passage corresponding portion 174_a_ to the crystallization temperature thereof or higher (that is, the metallic glass keeps amorphous and is not crystallized).

Further, it is preferable that a diametrical direction extending portion of the through-hole 180 configured by withdrawing the second core configuring element 178_b_ in the one end part 176_a_ with a large diameter of the ultrasonic transmission member 176 substantially coincides with a node of the ultrasonic wave input from the ultrasonic generator USG into the one end part 176_a_ of the ultrasonic transmission member 176.

Thereby, such a possibility can be remarkably reduced that a pipe member connected to an opening of the through-hole 180 in the outer peripheral surface of the one end part 176_a_ with a large diameter of the ultrasonic transmission member 176 as described later, is damaged by vibration of the ultrasonic wave input from the ultrasonic generator USG into the one end part 176_a_ of the ultrasonic transmission member 176.

Figure 15B:
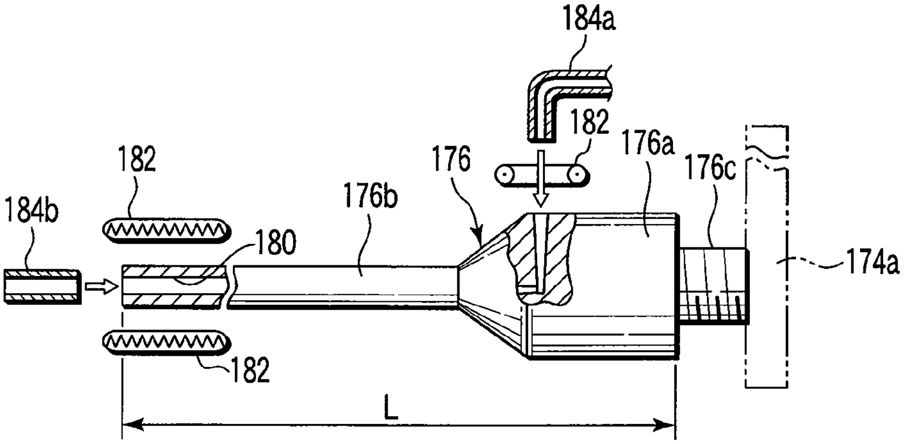
FIG. 15B is a side view schematically showing an ultrasonic transmission member formed with metallic glass by using the casting cavity of the main mold with the elongated and tapered core members shown in FIG. 15A, and pipe members to be connected to openings at both ends of a through-hole of the ultrasonic transmission member, in a state that parts of the ultrasonic transmission member and the pipe members are cut.
Figure 15C:
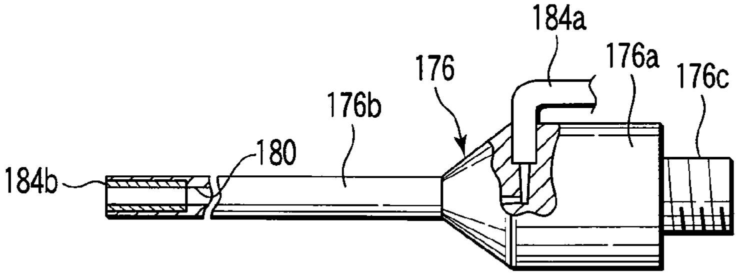
FIG. 15C is a side view schematically showing a state that the pipe members shown in FIG. 15B are connected to the openings at the both ends of the through-hole of the ultrasonic transmission member shown in FIG. 15B and the parts of the ultrasonic transmission member are cut.

Next, as shown in FIG. 15B, a surrounding of the opening of the through-hole 180 in the outer peripheral surface of the one end part 176_a_ with a large diameter of the ultrasonic transmission member 176 and the outer end portion of the other end part 176_b_ with a small diameter are heated by heaters 182, and they are heated and kept in a supercooled liquid region (a glass transition zone) of the metallic glass forming the ultrasonic transmission member 176. And, during this time, pipe members 184_a_ and 184_b_ having desired shapes are inserted into the opening of the through-hole 180 in the outer peripheral surface of the one end part 176_a_ with a large diameter of the ultrasonic transmission member 176 and an opening of the through-hole 180 in the outer end of the other end part 176_b_ with a small diameter.

It is preferable that each of the pipe members 184_a_ and 184_b_ is formed with a material which is not changed in quality by a fluid flowing in the through-hole 180, such as for example, titanium.

Thereafter, activation of the heaters 182 is stopped and the pipe members 184_a_ and 184_b_ having desired shapes are tightly placed in the inside of the opening of the through-hole 180 in the outer peripheral surface of the one end part 176_a_ with a large diameter of the ultrasonic transmission member 176 and in the inside of the opening of the through-hole 180 in the outer end of the other end part 176_b_ with a small diameter.

Here, as shown in FIG. 15B, insertion of the pipe members 184_a_ and 184_b_ into both of the opening of the through-hole 180 in the outer peripheral surface of the one end part 176_a_ with a large diameter of the ultrasonic transmission member 176 and the opening of the through-hole 180 in the outer end of the other end part 176_b_ with a small diameter and separation thereof from both of the openings can be performed repeatedly by heating the surrounding of the opening of the through-hole 180 in the outer peripheral surface of the one end part 176_a_ with a large diameter of the ultrasonic transmission member 176 and the outer end portion of the other end part 176_b_ by the heaters 182 to heat them to the supercooled liquid region (a glass transition zone) of the metallic glass forming the ultrasonic transmission member 176 and to keep their temperature in the supercooled liquid region (a glass transition zone).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic transmission member comprising:
a main body including a first end part, a second end part, and an outer peripheral surface, transmitting ultrasonic waves inputted at the first end part to the second end part, and formed of a metal glass,
a cross section of the first end part being larger than a cross section of the second end part,
the metal glass formed from an alloy comprising at least three elements including at least one of Ti, Zr, and Al, an element ration of Ti in the alloy ranging between more than or equal to 40% and less than or equal to 53%, and the element ratio of Zr in the alloy ranging between more than or equal to 55% and less than or equal to 60%,
a distance from an end of the first end part which is opposite to the second end part up to an end of the second end part which is opposite to the first end part being an integer multiple of a half of one wavelength of the ultrasonic wave, and
a starting position of transition from the first end part to the second end part on the outer peripheral surface of the main body substantially coinciding with a node of the ultrasonic wave.

2. The ultrasonic transmission member according to claim 1, wherein
the main body is provided with an ultrasonic slender probe including the first end part and the second end part at both end parts thereof.

3. The ultrasonic transmission member according to claim 2, wherein
a region of the second end part of the main body, which is located opposite to the first end part, is convertable to a desired shape.

4. The ultrasonic transmission member according to claim 1, wherein
the alloy from which the metal glass is formed is one of Zr55Cu30Al10Ni5, Zr60Cu30Al10, Ti53Cu30Ni15Co2, Al10Ni15La65Y10, Ti53Cu15Ni18.5Hf3Al7Si3B0.5, Ti40Zr10Cu36Pd14, and Ti53Cu15Ni18.5Zr3Al7Si3B0.5.

5. An ultrasonic transmission member comprising:
a main body including a first end part, a second end part, and an outer peripheral surface, transmitting ultrasonic waves inputted at the first end part to the second end part, and being formed of a metal glass; and
a U-shaped pipe having both end parts, and extending from the first end part to a position near to the distal end of the second end part and then returning to the first end part in the main body, both end parts of the U-shaped pipe being exposed in an outside of the outer peripheral surface at an area of the outer peripheral surface corresponding to the first end part,
the position on the first end part corresponding area of the outer peripheral surface, at which the both end parts of the U-shaped pipe are exposed in the outside of the outer peripheral surface, substantially coinciding with a node of the ultrasonic wave inputted in the first end part of the main body.

6. The ultrasonic transmission member according to claim 5, wherein the alloy from which the metal glass is formed is one of Zr55Cu30Al10Ni5, Zr60Cu30Al10, Ti53Cu30Ni15Co2, Al10Ni15La65Y10, Ti53Cu15Ni18.5Hf3Al7Si3B0.5, Ti40Zr10Cu36Pd14, and Ti53Cu15Ni18.5Zr3Al7Si3B0.5.

7. The ultrasonic transmission member according to claim 5, wherein the alloy which is the material of the metallic glass comprises at least three elements including at least one of Ti, Zr, and Al.

8. The ultrasonic transmission member according to claim 7, wherein the at least one included in the at least three elements of the alloy from which the metal glass is formed is one of Ti and Zr, an element ratio of Ti in the alloy ranging between more than or equal to 40% and less than or equal to 53%, and the element ratio of Zr in the alloy ranging between more than or equal to 55% and less than or equal to 60%.

* * * * *